US009994866B2

(12) United States Patent
Jostock et al.

(10) Patent No.: US 9,994,866 B2
(45) Date of Patent: Jun. 12, 2018

(54) EXPRESSION VECTOR SYSTEM COMPRISING TWO SELECTION MARKERS

(71) Applicant: NOVARTIS AG, Basel (CH)

(72) Inventors: Thomas Jostock, Neuenburg am Rhein (DE); Hans-Peter Knopf, Schallstadt (DE)

(73) Assignee: NOVARTIS AG, Basel (CH)

( * ) Notice: Subject to any disclaimer, the term of this patent is extended or adjusted under 35 U.S.C. 154(b) by 0 days. days.

(21) Appl. No.: 15/356,748

(22) Filed: Nov. 21, 2016

(65) Prior Publication Data

US 2017/0067077 A1   Mar. 9, 2017

Related U.S. Application Data

(62) Division of application No. 13/203,610, filed as application No. PCT/EP2010/001224 on Feb. 26, 2010, now Pat. No. 9,534,226.

(30) Foreign Application Priority Data

Feb. 27, 2009  (EP) ..................... 09153995

(51) Int. Cl.
  C12N 15/85   (2006.01)
  C12N 15/52   (2006.01)
  C12N 9/06    (2006.01)
  C12P 21/02   (2006.01)
  C12N 1/20    (2006.01)
  C12N 15/79   (2006.01)

(52) U.S. Cl.
  CPC .............. C12N 15/85 (2013.01); C12N 1/20 (2013.01); C12N 9/003 (2013.01); C12N 15/52 (2013.01); C12N 15/79 (2013.01); C12P 21/02 (2013.01); C12Y 105/01003 (2013.01); C12N 2800/40 (2013.01)

(58) Field of Classification Search
  None
  See application file for complete search history.

(56) References Cited

U.S. PATENT DOCUMENTS

| 5,830,698 A | 11/1998 | Reff et al. |
| 5,879,686 A | 3/1999 | Blake |
| 2004/0148647 A1 | 7/2004 | Enenkel et al. |

FOREIGN PATENT DOCUMENTS

| CA | 2507714 A1 | 6/2004 |
| EP | 0724639 B1 | 2/1992 |
| WO | 2004/081167 A | 9/2004 |
| WO | 2005/073375 A1 | 8/2005 |
| WO | 2007096399 A2 | 8/2007 |
| WO | 2007/131774 A1 | 11/2007 |
| WO | 2010/022961 A1 | 3/2010 |
| WO | 2010097240 A1 | 9/2010 |

OTHER PUBLICATIONS

Folate receptor 1 precursor [*Homo sapiens*], NCBI Reference Sequence: NP_00793.1, www.ncbi.nlm.nih.gov/protein/4758400?sat=12&satkey=2867627, p. 1-3, Feb. 11, 2008.
Spandidos, et al: "Linkage of markers controlling consecutive biochemical steps inb CHO cells as demonstrated by chromosome transfer", Cell, vol. 12, pp. 235-242, Sep. 1997.
Spinella, et al: "Comparison of methotrexate polyglutamylation L1210 leukemia cells with influx is mediated by the reduced folate carrier or the folate receptor; lack of evidence for influx route-specific effects" Biochemical Pharmacology; , vol. 52, pp. 703-712, (1996).
Rothem L et al: "The reduced folate carrier gene is a novel selectable marker for recombinant protein overexpression", Molecular Pharmacology, American Society for Pharmacology and Experimental Therapeutics, Baltimore, MD vol. 62, No. 3, pp. 616-624, 2005.
Zhu Wei-Yong et al: The rate of folate receptor alpha (FRalpha) synthesis in folate depleted CHL cells is regulated by a translational mechanism sensitive to media folate levels while stable overexpression of its mRNA is mediate by gene amplification and an increase in transcript half-life, Journal of Cellular Biochemistry, Viley-Liss Inc., US, vol. 81, No. 2, pp. 205-219, 2001.
Salazar M D et al: "The folate receptor: what does it promise in tissue-targeted therapeutics?", Cancer Metastasis Rev. 26(1), pp. 141-152, 2007.
Grillari J et al: "Analysis of alternations in gene expression after amplification of recombinant genes in CHO cells", Journal of Biotechnol. 87, pp. 59-65 2001.
Levitt N et al: "Definition of an efficient synthetic poly(A) site"< Genes & Development 3(7), pp. 1019-1025, 1989.
Subramani S et al: "Expression of the mouse dihydrofolate reductase complementary deoxyribonucleic acid in simian virus 40 vectors", Molecular and Cellular Biology, 1(9), pp. 854-865, 1981.
Eaton D et al: "Construction and characterization of an active factor viii variant lacking the central one-third of molecule", Biochemistry 25(25) pp. 8343-8347, 1986.
Neuberger M: "Expression and regulation of immunoglobulinheavy chain gene transfected into lymphoid cells", the EMBO Journal 2(8), pp. 1373-1378, 1983.

(Continued)

*Primary Examiner* — Antonio Galisteo Gonzalez
(74) *Attorney, Agent, or Firm* — Jason J. Derry

(57) ABSTRACT

The invention pertains to an expression vector or a combination of at least two expression vectors comprising at least
  (a) a polynucleotide encoding a product of interest or an insertion site for incorporating a polynucleotide encoding a product of interest;
  (b) a polynucleotide encoding a first selectable marker (sm I);
  (c) a polynucleotide encoding a second selectable marker (sm II), which is different from the first selectable marker (sm I),
wherein the activity of the selectable marker (sm I) or (sm II) is at least partially influenced by the activity of the other selectable marker and wherein the selectable markers (sm I) and (sm II) are involved in the folate metabolism. Also provided are suitable host cells, selection methods and methods for producing polypeptides with high yield.

12 Claims, No Drawings

(56) References Cited

OTHER PUBLICATIONS

Oumard A et al: "Recommended method for chromosome exploitation: RMCE-based cassette-exchange systems in animal cell biotechnology", Cytotechnology 50, pp. 93-108, 2006.
Sorrell D et al: "Targeted modification of mammalian genomes", Biotechnology Advances 22, pp. 431-469, 2005.
Wurm F.: "Production of recombinant protein therapetuics in cultivated mammalian cells", Nature Biotechnology 22(11) pp. 393-1398, 2004.

EXPRESSION VECTOR SYSTEM COMPRISING TWO SELECTION MARKERS

FIELD OF THE INVENTION

The present invention relates to a novel selection system suitable for selecting host cells, in particular mammalian host cells, expressing a product of interest. Said selection system is based on the use of at least two selectable markers (sm I and sm II) wherein the activity of the selectable marker (sm I) or (sm II) is at least partially influenced by the activity of the other selectable marker. The invention provides suitable expression vectors, host cells and methods for selecting host cells expressing a product of interest with a high yield. Furthermore, the present invention pertains to a method for efficiently producing polypeptides with a high yield.

BACKGROUND OF THE INVENTION

The ability to clone and express products of interest such as recombinant peptides and proteins in large amounts has become increasingly important. The ability to purify high levels of proteins is important in the human pharmaceutical and biotechnological field, for example for producing protein pharmaceuticals as well as in the basic research setting, for example for crystallizing proteins to allow the determination of their three dimensional structure. Proteins that are otherwise difficult to obtain in quantity can be over-expressed in a host cell and subsequently isolated and purified.

The choice of an expression system for the production of recombinant proteins depends on many factors, including cell growth characteristics, expression levels, intracellular and extracellular expression, post-translational modifications and biological activity of the protein of interest, as well as regulatory issues and economic considerations in the production of therapeutic proteins. Key advantages of mammalian cells over other expression systems such as bacteria or yeast are the ability to carry out proper protein folding, complex N-linked glycosylation and authentic O-linked glycosylation, as well as a broad spectrum of other post-translational modifications. Due to the described advantages, eukaryotic and in particular mammalian cells are currently the expression system of choice for producing complex therapeutic proteins such as monoclonal antibodies.

The most common approach to obtain high expressing host cells (also called high producers) generates an appropriate expression vector for expressing the product of interest as a first step. The expression vector drives the expression of the polynucleotide encoding the product of interest in the host cell and provides at least one selectable marker for generating the recombinant cell line. Key elements of mammalian expression vectors usually include a constitutive or inducible promoter capable of robust transcriptional activity; optimized mRNA processing and translational signals that usually include a Kozak sequence, a translation termination codon, mRNA cleavage and polyadenylation signals, a transcription terminator and selectable markers for the preparation of stable cell lines and for gene amplification; furthermore a prokaryotic origin of replication and selectable markers for vector propagation in bacteria can be provided by the expression vector.

In recent years the focus of development was concentrating on the design of improved vectors for gene expression in host and in particular in mammalian cells. Despite of the plethora of available vectors, however, robust polypeptide/protein production with a high yield in mammalian cells is still challenging.

One established procedure for obtaining high producing cell lines expressing the product of interest with high yield is the stable transfection of the host cells. However, the stable integration into the genome is a rare event and only a small subset of stably transfected cells are high producers.

Selectable markers and selection systems are widely used in genetic engineering, recombinant DNA technology and the production of recombinant products in order to obtain host cells expressing the product of interest with high yield. Respective systems are also useful to generate and identify stably transfected clones. The primary goal of using respective selectable markers and selection systems is to introduce a selectable gene which upon exposure to selective growth conditions allows the identification of cells capable of high-level production of the recombinant products of interest. Increasing the yield of product expression can be e.g. achieved by gene amplification using cells lines e.g. deficient in an enzyme such as dihydrofolate reductase (DHFR) or glutamine synthetase (GS) in conjunction with expression vectors containing genes encoding these selectable marker enzymes and agents such as methotrexate (MTX), which inhibits DHFR, and methionine sulfoxamine (MSX) which inhibits GS. Also more sensitive mutant forms of the respective selectable markers can be used in conjunction with wildtype cells. Using expression vectors containing the recombinant gene under control of a strong promoter and genes encoding selectable markers such as DHFR or GS, $DHFR^+$ (plus) or $GS^+$ (plus) transfectants, respectively, are first obtained and gene amplification is then achieved by growing the transfectants in progressively increasing concentrations of MTX or MSX. The aim of providing such a selection pressure is to isolate cells that express the selectable markers and accordingly, the product of interest with a high yield.

Therefore, a high stringency selection system is crucial to enrich high producing cells from the transfected population. The higher the stringency of the selection system the lower the number of low producers after the selection process and the higher the chance to find the very rare ultra high producing clones.

It is the object of the present invention to provide a stringent selection system for selecting host cells producing a product of interest with high yield, as well as suitable expression vectors and host cells.

SUMMARY OF THE INVENTION

The present invention pertains to a selection system for selecting host cells expressing a product of interest with a high yield and to the production of respective products, in particular polypeptides.

According to one embodiment, the present invention pertains to an expression vector or a combination of at least two expression vectors comprising at least
  (a) a polynucleotide encoding a product of interest or an insertion site for incorporating a polynucleotide encoding a product of interest;
  (b) a polynucleotide encoding a first selectable marker (sm I);
  (c) a polynucleotide encoding a second selectable marker (sm II), which differs from the first selectable marker (sm I),
wherein the activity of the selectable marker (sm I) or (sm II) is at least partially influenced by the activity of the other selectable marker and wherein the selectable markers (sm I) and (sm II) are involved in the folate metabolism.

The present invention further relates to a host cell, in particular a mammalian host cell, comprising at least
  (a) an introduced polynucleotide encoding a product of interest;
  (b) an introduced polynucleotide encoding a first selectable marker (sm I);
  (c) an introduced polynucleotide encoding a second selectable marker (sm II), which differs from the first selectable marker (sm I);
wherein the activity of the selectable marker (sm I) or (sm II) is at least partially influenced by the activity of the other selectable marker and wherein the selectable markers (sm I) and (sm II) are involved in the folate metabolism.

Furthermore, a method is provided for selecting at least one host cell capable of expressing a product of interest, comprising
  (a) providing a plurality of host cells, comprising at least
    (i) an introduced polynucleotide encoding a product of interest;
    (ii) an introduced polynucleotide encoding a first selectable marker (sm I);
    (iii) an introduced polynucleotide encoding a second selectable marker (sm II); which differs from the first selectable marker (sm I);
    wherein the activity of the selectable marker (sm I) or (sm II) is at least partially influenced by the activity of the other selectable marker and wherein the selectable markers (sm I) and (sm II) are involved in the folate metabolism;
  (b) culturing said plurality of host cells under growth conditions selective for the selectable markers (sm I) and (sm II), thereby obtaining a host cell expressing the product of interest.

Also provided is a selective culture medium that can be used in the selection method according to the present invention which comprises folate in a limiting concentration and an antifolate. A "selective culture medium" is a cell culture medium useful for the selection of host cells.

The invention also relates to a process for producing a product of interest, comprising culturing a host cell according to the present invention or a host cell selected according to the teachings of the present invention under conditions that allow for the expression of the product of interest.

The invention also pertains to the use of a first selectable marker (sm I) in combination with a second selectable marker (sm II), which differs from the first selectable marker (sm I). The activity of the selectable marker (sm I) or (sm II) is at least partially influenced by the activity of the other selectable marker, for selecting a eukaryotic, in particular a mammalian host cell expressing a product of interest. The selectable markers (sm I) and (sm II) are preferably involved in the same or a concerted metabolic process or pathway essential for cell viability or cell proliferation. Preferably, the selectable markers (sm I) and (sm II) are involved in the folate metabolism.

The strategy of the present invention to use two selectable markers (sm I) and (sm II) wherein the activity of the selectable marker (sm I) or (sm II) is at least partially influenced by the activity of the other selectable marker and wherein both selectable markers (sm I) and (sm II) are involved in the same metabolic pathway essential for cell viability or cell proliferation results in very stringent selection conditions. This will be explained here on the basis of the preferred embodiment wherein both selection markers (sm I) and (sm II) are involved in the folate mechanism. The folate metabolism is an essential metabolic pathway that is crucial for cell survival and cell growth. As the activity of the selectable marker (sm I) or (sm II) influences the activity of the other selectable marker and both selection markers are involved in the folate metabolism, the folate metabolism functions under selective culture conditions only effective, if both selection markers (sm I) and (sm II) are expressed in sufficient amounts and accordingly, are expressed with a high yield in the recipient host cell. Thereby, the selection pressure on the host cells is remarkably increased.

In a preferred embodiment which also explains how the activity of the selectable marker (sm II) is at least partially influenced by the activity of the selectable marker (sm I), the selectable marker (sm I) is or comprises a transporter polypeptide which incorporates a folate into the host cell. The selectable marker (sm II) is a catalytic polypeptide processing as substrate the folate incorporated by the selectable marker (sm I) or a subsequent product obtained or generated from said imported folate. A preferred example of a respective catalytic polypeptide is DHFR. It is believed that in this embodiment, the second selectable marker (sm II) operates with a higher efficiency or a higher turnover rate, if the folate transporter (sm I) incorporates sufficient amounts of folate into the host cells. Without being bound by theory, it is believed that a strong expression of the folate transporter as first selectable marker (sm I) allows the host cells to import more folate from the culture medium into that cell and accordingly, allows the host cells to tolerate lower concentrations of folate in the culture medium. A strong expression of the folate transporter (sm I) results in that sufficient substrate for the catalytic polypeptide (sm II) (or precursor of said substrate) is imported into the host cell and thus is available for the catalytic polypeptide (sm II). Thus, the activity of the catalytic polypeptide (sm II) is influenced by the activity of the folate transporter (sm I), as the activity of the catalytic polypeptide (sm II) depends on that sufficient amounts of folate are imported into the host cell by the folate transporter (sm I). Therefore, the cell viability is maintained/increased in case the host cell strongly expresses the first selectable marker (sm I) and thus imports sufficient amounts of folate into the cell in order to keep up the folate metabolism, even if the concentration of folate in the culture medium is very low. Due to the activity of the folate transporter (sm I), the availability of the substrate for the catalytic polypeptide (sm II) is increased. The selective culture medium may comprise an inhibitor of the catalytic polypeptide (sm II), e.g. a competitor of its actual substrate. Cells strongly expressing the catalytic polypeptide (sm II) tolerate higher concentrations of said inhibitor, especially at high substrate concentrations, said concentration being at least partially dependent on the activity of the folate transporter used as selectable marker (sm I). This coupling of the activity/functionality of the selectable markers (sm I) and (sm II) has the effect that the host cell's viability and/or growth rate is considerably increased under selective culture conditions, if both selectable markers (sm I) and (sm II) are strongly expressed. Host cells survive/proliferate that despite the selective culture conditions can keep up the folate metabolism sufficiently in order to allow cell survival and growth.

The unique design of the expression system according to the present invention provides a very stringent selection system allowing the enrichment of high producing cells from the transfected host cell population. This high stringency of the selection system according to the present invention lowers the number of low producers in the population after selection and increases the chance to find the very rare ultrahigh producing clones. This increases the productivity of the cell population surviving selection. The examples show that the host cells obtained with the selection system according to the present invention produce the product of interest with a high yield. Also the average productivity of the individual producer clones is increased. Thus, the selection system according to the present invention increases the chances to find high producer clones with lower screening efforts.

The above assumptions reflect the current understanding of the underlying mechanism but are, however not binding as there may be other explanations for the observed dependency/increase in the selection pressure when using selectable markers (sm I) and (sm II) that are both involved in the folate metabolism. Furthermore, as is also outlined in the detailed description, the general principle of the present invention is also applicable to other metabolic processes or pathways and other selectable markers (sm I) and (sm II). However, it is important that the activity of the selectable marker (sm I) or (sm II) is at least partially influenced by and in particular is dependent on the activity of the other selectable marker in order to increase the selection pressure. Thus, other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

According to one aspect of the present invention, an expression vector or a combination of at least two expression vectors is provided, comprising at least
(a) a polynucleotide encoding a product of interest or an insertion site for incorporating a polynucleotide encoding a product of interest;
(b) a polynucleotide encoding a first selectable marker (sm I);
(c) a polynucleotide encoding a second selectable marker (sm II), which differs from the first selectable marker (sm I),
wherein the activity of the selectable marker (sm I) or (sm II) is at least partially influenced by the activity of the other selectable marker.

A "selectable marker" (sm) which is expressed by the introduced polynucleotide allows under appropriate selective culture conditions the selection of host cells expressing said selectable marker. A selectable marker is preferably a biomolecule, in particular a polypeptide. Suitable selectable markers are described in detail below.

A "vector" according to the present invention is a polynucleotide capable of carrying at least one polynucleotide fragment. A vector functions like a molecular carrier, delivering fragments of nucleic acids respectively polynucleotides into a host cell. It may comprise at least one expression cassette comprising regulatory sequences for properly expressing a polynucleotide incorporated therein. Polynucleotides (e.g. encoding the product of interest or selectable markers) to be introduced into the cell may be inserted into the expression cassette(s) of the vector in order to be expressed therefrom. The vector according to the present invention may be present in circular or linear(ized) form and also encompasses vector fragments. The term "vector" also comprises artificial chromosomes or similar respective polynucleotides allowing the transfer of foreign nucleic acid fragments.

A "polynucleotide" is a polymer of nucleotides which are usually linked from one deoxyribose or ribose to another and refers to DNA as well as RNA, depending on the context. The term "polynucleotide" does not comprise any size restrictions and also encompasses polynucleotides comprising modifications, in particular modified nucleotides.

An "introduced polynucleotide" refers to a polynucleotide that has been introduced into a host cell e.g. by the use of recombinant techniques such as transfection. The host cell may or may not comprise an endogenous polynucleotide corresponding to, respectively being identical to the introduced polynucleotide. Introduction may be achieved e.g. by transfecting a suitable vector that may integrate into the genome of the host cell (stable transfection). Suitable vectors allowing the introduction of polynucleotides into the host cell are described in detail below. In case the introduced polynucleotide is not inserted into the genome, the introduced polynucleotide can be lost at the later stage e.g. when the cells undergo mitosis (transient transfection). Suitable vectors might also be maintained in the host cell without integrating into the genome, e.g. by episomal replication. However, also other techniques are known in the prior art for introducing a polynucleotide into a host cell which are described in further detail below.

A "product of interest" refers to the product to be expressed in said host cell. The product of interest may be e.g. a polypeptide or a polynucleotide, such as RNA. Preferably, the product of interest is a polypeptide, in particular an immunoglobulin molecule. Examples are described below.

A "polypeptide" refers to a molecule comprising a polymer of amino acids linked together by a peptide bond(s). Polypeptides include polypeptides of any length, including proteins (for example, having more than 50 amino acids) and peptides (for example, having 2-49 amino acids). Polypeptides include proteins and/or peptides of any activity or bioactivity. Suitable examples are outlined below.

The feature, that the "activity of the selectable marker (sm I) or (sm II) is at least partially influenced by the activity of the other selectable marker" particularly means that the activity of one selectable marker is influenced by and/or depends at least to a certain degree directly or indirectly on the activity respectively function of the other selectable marker (and optionally vice versa). "Activity" in this context particularly describes any function or action of the selectable marker that provides, promotes and/or increases resistance to the selective pressure and includes but is not limited to the catalytic activity, the turnover rate, the kinetic reaction rate and/or the transportation rate of the selectable marker. This dependency/interaction of the selectable markers (sm I) and (sm II) can considerably increase the selection pressure on the host cells under selective culture conditions. Preferably, the selectable marker (sm I) and the selectable marker (sm II) are involved in the same or a concerted metabolic process or pathway essential for cell viability or proliferation. Suitable examples of selectable markers (sm I) and (sm II) and metabolic processes and pathways are described in detail below.

Subsequently, we describe embodiments and advantages of the expression vector or combinations of expression vectors according to the present invention. Where appropriate, we describe these advantages in conjunction with the use of said expression vector(s) in selecting host cells expressing the product of interest.

According to the teachings of the present invention, the activity of the selectable marker (sm I) or (sm II) is influenced by and accordingly is at least partially dependent on the activity of the other selectable marker under culture conditions selective for both selectable markers. Due to this interaction of the selectable markers (sm I) and (sm II), the selective pressure on the host cells is increased. Due to its unique design, a very stringent selection system is provided allowing the enrichment of high producing cells from the transfected host cell population. This high stringency of the selection system according to the present invention lowers the number of low producers in the population after selection and increases the chance to find the very rare ultrahigh producing clones.

According to a preferred embodiment, the selectable markers (sm I) and (sm II) are both involved in the same metabolic process which is preferably essential for cell viability and/or proliferation; e.g. the synthesis of nucleic acids or polypeptides. Thus, when the expression vector or the combination of at least two expression vectors is introduced into the recipient host cell, the activity/presence of said selectable markers (sm I) and (sm II) in conjunction with the selective culture conditions influence/attack the same metabolic process of the recipient host cell. Accordingly, the activity of the selectable markers (sm I) and (sm II) influence each other within said metabolic process, thereby increasing the selection pressure on the host cell. Host cells survive/proliferate under selective culture conditions that despite the selective culture conditions can keep up said metabolic process sufficiently in order to allow cell survival and growth. Survival/growth is promoted if said host cells express both selectable markers (sm I) and (sm II) and accordingly the introduced expression vector(s) with high yield. Thereby, host cells are selected which also express the product of interest with high yield.

A "metabolic process" particularly describes a process in the host cell, which is essential for cell viability and/or cell proliferation. Examples of metabolic processes are nucleic acid synthesis or polypeptide synthesis. A "metabolic pathway" in particular refers to a subgroup of a metabolic process and describes a defined series of chemical reactions occurring within a cell. In each pathway, a principal chemical is modified by chemical reactions. A classical example of a metabolic pathway is the nucleotide synthesis (belonging to the metabolic process of nucleic acid synthesis), in particular the purine or pyrimidine biosynthesis, or the synthesis of amino acids (belonging to the metabolic process of polypeptide synthesis). There are several levels of metabolic pathways, which are also often interdependent and thus connected. Therefore, these terms are to be understood rather functionally as the individual metabolic pathways and also metabolic processes often overlap.

According to one embodiment, the first selectable marker (sm I) and/or the second selectable marker (sm II) is involved in a metabolic process or pathway which is selected from
a) nucleic acid synthesis and/or polypeptide synthesis,
b) nucleotide synthesis and/or amino acid synthesis, and
c) the folate metabolism.

The mentioned metabolic processes/pathways are important for maintaining the cellular viability of the host cell and/or for the proliferation of the host cells. Therefore, they are suitable working points for the selection system according to the present invention. Thus, these metabolic pathways are very suitable for choosing appropriate selection markers involved therein as selectable marker (sm I) and selectable marker (sm II) and suitable selection conditions allowing the selection of host cells expressing said markers. Suitable selection markers involved in the respective metabolic pathways as well as suitable host cells and suitable selection conditions are known in the prior art and are described below and can thus be used in conjunction with the present invention.

According to one embodiment, the first selectable marker (sm I) and/or the second selectable marker (sm II) is a eukaryotic selectable marker. A "eukaryotic selectable marker" allows the selection of eukaryotic host cells comprising respectively expressing said selectable marker. Said eukaryotic selectable marker can be a metabolic selectable marker and thus a marker that is involved in a metabolic process or pathway of the cell, e.g. nucleic acid or polypeptide synthesis.

Furthermore, the first selectable marker (sm I) and/or the second selectable marker (sm II) can be an amplifiable selectable marker. An amplifiable selectable marker allows the selection of vector containing host cells and promotes gene amplification. Examples of respective amplifiable selectable markers are known in the prior art such as DHFR and GS.

The first selectable marker (sm I) and/or the second selectable marker (sm II) can be a catalytic polypeptide or a transporter polypeptide. Many suitable respective selectable markers exist that can be used in conjunction with the present invention and will be explained in detail below.

According to one embodiment, the second selectable marker (sm II) is a catalytic polypeptide processing
  (a) a substrate which is a compound that is incorporated by the first selectable marker (sm I) into the host cell or a subsequent product obtained from said incorporated compound and/or
  (b) a substrate which, or a precursor of which, is obtained by the activity of the first selectable marker (sm I).

Hence, said catalytic polypeptide used as a selectable marker (sm II) may process a substrate that is imported into the host cell by the activity of the first selectable marker (sm I). It may also process a substrate that is produced by the activity of the first selectable marker (sm I). Said compound that is e.g. incorporated into the host cell by the first selectable marker (sm I) can also be a precursor of the actual substrate that is processed by the second selectable marker (sm II). Thus, the catalytic polypeptide (sm II) may also process a substrate that is a subsequent product obtained from the compound that is incorporated into the host cell by the activity first selectable marker (sm I). The same applies in case the selectable marker (sm I) is a catalytic polypeptide instead of a transporter polypeptide.

Without being bound by theory, it is assumed that in this embodiment, the activity of the second selectable marker (sm II) strongly depends on the activity of the first selectable marker (sm I) under culture conditions selective for both markers. The presence and/or amount of substrate for the second selectable marker (sm II) depends at least to a certain degree on the proper expression/activity of the selectable marker (sm I). Strong overexpression of the first selectable marker (sm I), leads to a higher availability of substrate for the second selectable marker (sm II). The higher availability of the substrate increases the activity of the second selectable marker (e.g. the turnover rate). However, if the selectable marker (sm I) is not expressed with a sufficient yield, no or less substrate is generated for the selectable marker (sm II), whose activity accordingly also decreases.

According to one embodiment, the first selectable marker (sm I) is a transporter polypeptide responsible for introducing/incorporating a compound from the culture medium into the host cell, which is the substrate or a precursor of a substrate of the second selectable marker (sm II). Preferably, said compound is essential for cell viability and/or proliferation. It is believed that in this embodiment, the second selectable marker (sm II) operates with a higher efficiency or turnover rate, if the first selectable marker (sm I) incorporates sufficient amounts of said compound into the host cells. Without being bound by theory, it is believed that a strong overexpression of the first selectable marker (sm I) allows the host cells to import more of said compound from the culture medium into that cell and accordingly, allows the host cells to tolerate lower concentrations of said compound in the culture medium. This also leads to a higher availability of said compound and accordingly substrate (or precursor of said substrate) of the second selectable marker (sm II) in the host cell. The same principles apply in case the first selectable marker (sm I) is a catalytic polypeptide producing a substrate or a precursor of a substrate that is processed/used by the second selectable marker (sm II). This assumption reflects the current understanding of the underlying mechanism but is, however not binding as there may be other explanations for the observed dependency/increase in the selection pressure.

The activity of the selectable markers (sm I) or (sm II) influences the activity of the other selectable marker and both target the same or a concerned metabolic process or pathway, e.g. nucleotide synthesis or folate metabolism, which accordingly functions more effective under selective culture conditions, if both selection markers are expressed in sufficient amounts and accordingly, are expressed with a high yield in the host cell. This results in highly stringent selection conditions.

According to one embodiment, the first selectable marker (sm I) operates upstream of the second selectable marker (sm II). This means, that e.g. within the same or concerted metabolic pathway, the first selectable marker (sm I) may e.g. operate at the beginning of said pathway and the second selectable marker (sm II) operates downstream of the selectable marker (sm I).

According to a preferred embodiment, the first selectable marker (sm I) is or comprises a transporter polypeptide. A "transporter polypeptide" is in particular a polypeptide mediating the transfer of a compound from one compartment to another, in particular from the culture medium into the host cell. Examples of suitable transporter polypeptides include receptor polypeptides, channels and carriers.

As a transporter polypeptide, said selectable marker (sm I) preferably imports a compound into the host cell that is involved in and/or is essential for the cellular viability or proliferation of the host cell. Thus, cell viability or proliferation depends at least partially on the import of said compound into the host cell. The second selectable marker (sm II) used in combination with the transporter polypeptide (sm I) is preferably an enzyme which is involved in a metabolic pathway or process that is dependent/influenced by the transporter activity of the first selectable marker (sm I), as it makes e.g. use of the imported compound or a subsequent product thereof. In this embodiment, the activity and in particular the turnover rate of said second selectable marker (sm II) at least partially depends on the activity of the transporter polypeptide (sm I), which imports said compound into the host cell. In conjunction with this embodiment, a selective culture medium can be used which comprises a limiting concentration of said compound that is imported by the transporter polypeptide (sm I) into the host cell.

A "limiting concentration" refers to a concentration of said compound in the selective culture medium which provides a selective pressure on the host cell. Accordingly, said compound is not comprised in the selective culture medium in affluence, thereby providing a selection pressure on the host cells. Thus, the selective culture medium may e.g. be deprived of, respectively may contain low amounts of said compound that is incorporated/transported by the transporter polypeptide (sm I) into the cell.

Therefore, the cell viability is maintained/increased in case the host cell over-expresses the first selectable marker (sm I) and thus imports sufficient amounts of said compound into the cell in order to keep up the concerned metabolic pathway, even if the concentration of said compound in the culture medium is very low. If the expression and accordingly the activity of the transporter polypeptide (sm I) is increased, the availability of the substrate for the second selectable marker (sm II) is increased. When the second selectable marker (sm II) is a catalytic polypeptide, the selective culture medium may comprise an inhibitor of said second selectable marker (sm II), e.g. a competitor of the actual substrate of the second selectable marker (sm II). Cells strongly overexpressing the second selectable marker (sm II) tolerate higher concentrations of said inhibitor, especially at high substrate concentrations (which is at least partially dependent on the activity of the selectable marker (sm I)). This has the effect that the host cell's viability is considerably increased under selective conditions, if both selectable markers (sm I) and (sm II) are strongly expressed. Thereby, the expression rate of the product of interest is increased. Thus, the coupling of the activity/functionality of the selectable markers (sm I) and (sm II) results in very stringent selection conditions which allow the selection of high and also ultra-high expressing cell clones. The same principle applies in case the first selectable marker (sm I) is an enzyme involved in the production/generation of the substrate for the second selectable marker (sm II) (see above).

According to a preferred embodiment, the first selectable marker (sm I) and the second selectable marker (sm II) are involved in the folate metabolism. A folate according to the present invention can e.g. be an oxidized folate (i.e. folic acid) or a reduced folate or a derivative thereof. In general, a folate is useful within the present invention as long as such folate will be capable of being taken up into a host cell, in particular a mammalian host cell. The oxidized folate, i.e. folic acid, as well as reduced derivatives of folic acid, known as reduced folates or tetrahydrofolates (THF), are a group of B-9 vitamins that are essential cofactors and/or coenzymes for the biosynthesis of purines, thymidylate and certain amino acids in eukaryotic, in particular mammalian, cells. THF cofactors are particularly crucial for DNA replication and hence cellular proliferation. Specifically, THF cofactors function as donors of one-carbon units in a series of interconnected metabolic pathways involving de novo biosynthesis of purines and thymidylate, amino acids as well as methyl group metabolism, including CpG island methylation of DNA. Specifically, THF cofactors including 10-formyl-THF (10-CHO-THF) contribute one-carbon units in two key de novo formyltransferase reactions involved in the de novo biosynthesis of purines. A preferred example of an oxidized folate is folic acid. Preferred examples of reduced folates are 5-methyl-tetrahydrofolic acid, 5-formyltetrahydrofolic, 10-formyl-tetrahydrofolic acid and 5,10-methylene-tetrahydrofolic acid.

In contrast to most prokaryotes, plants and fungi which synthesize their own folates, mammals and other eukaryotic species are devoid of THF cofactor biosynthesis and must therefore obtain them from exogenous sources, usually the culture medium. Three independent transport systems are currently known to mediate the uptake of folates and antifolates in mammalian cells:

a) The predominant cellular transport system of reduced folate cofactors is the reduced folate carrier (RFC). The RFC (also known as solute carrier family 19 member 1, SLC19A1) is a ubiquitously expressed ~85 kDa membrane glycoprotein functioning as a bi-directional facilitative carrier that mediates the uphill transport of reduced folates by exchanging organic phosphates such as adenine nucleotides that are known to accumulate to very high intracellular levels as well as thiamine mono- and pyrophosphate. RFC displays a high-affinity for THF cofactors including leucovorin (5-formyl-THF; Kt=1 μM), while harbouring only a very poor transport affinity (Kt=200-400 μM) for folic acid, an oxidized folate.

b) Another route of folate uptake is the proton-coupled folate transporter (PCFT, also known as SLC46A) which has recently been cloned. PCFT appears to be expressed independently of the RFC, functions optimally at acidic pH (5.5) and mediates the influx of both oxidized (e.g. folic acid) and THF cofactors (i.e. reduced folates) as well as various hydrophilic antifolates including MTX. PCFT, which shows an optimal transport of folates and antifolates at acidic pH (5.5) but none at physiological pH (7.4), has a key role in the absorption of both folates and antifolates in the upper small intestine.

c) The third transport route involves folate receptors (FRs). FRs are high-affinity folate-binding glycoproteins encoded by three distinct genes FR alpha, FR beta and FR gamma. FR alpha is also known as Adult Folate Binding Protein or FDP, as Folate Receptor1 or FOLR (in mice folbp1), and as Ovarian cancer-Associated Antigen or MOv 18. FR beta is also known as FOLR2 (fetal) and as FBP/PL-1(placenta). FR gamma is also known as FOLR3 and as FR-G (reviewed by M. D. Salazar and M. Ratnam, Cancer Metastasis Rev. 2007 26(1), pp. 141-52.). The mature FRs, which are well-characterized, are homologous proteins with ~70-80% amino acid identity and contain 229 to 236 amino acids as well as two to three N-glycosylation sites. FR alpha and FR beta are membrane-bound, in particular glycosylphosphatidylinositol (GPI)-anchored, cell surface glycoproteins, whereas FR gamma is devoid of a GPI anchor and is a secreted protein. FR alpha and FR beta display a high affinity for folic acid (Kd=0.1-1 nM), 5,10-dideazatetrahydrofolic acid (DDATHF; lometrexol; Ki=0.4-1.3 nM using [$^3$H] folic acid as a substrate) and BGC945 (which is a cyclopenta[g]quinazoline-based, thymidylate synthase inhibitor specifically transported solely via FRalpha and not via the reduced folate carrier) (Kd=1 nM), but much lower affinity for MTX (Kd>100 nM). FR-dependent uptake of folate and antifolates proceeds via a classical mechanism of receptor-mediated endocytosis.

According to one embodiment, the first selectable marker (sm I) is a transporter polypeptide, which imports at least one folate from the culture medium into the host cell. In general, a folate is useful within the present invention as long as such folate will be capable of being taken up into a host cell, in particular a mammalian host cell, by the first selectable marker (sm I).

According to one embodiment, the first selectable marker (sm I) is or comprises the reduced folate carrier (RFC), or a functional variant or fragment thereof. RFC is a ubiquitously expressed membrane glycoprotein that serves as the major transporter for the uptake of reduced folates such as 5-methyl-THF and 5-formyl-THF into the cell. However, RFC displays a very poor affinity for the oxidized folate, folic acid. Hence, cells that lack the expression of RFC or have been deleted from the genomic RFC locus can serve as recipients for the transfection of the selectable marker gene RFC (as (sm I)) under conditions in which reduced folates such as 5-formyl-THF are gradually deprived from the growth medium, thereby forcing the cells to express increased levels of the this folate transporter.

According to a preferred embodiment which is also described in detail in the example section, the first selectable marker (sm I) is or comprises a folate transporter polypeptide and preferably, is a functional folate receptor. The use of a folate receptor or a functional variant or fragment thereof has several advantages over the use of the RFC selection system. It is not necessary to use cells, wherein the endogenous FR locus has been knocked out or inactivated by targeted knockout or loss of function mutations. Furthermore, RFC has a poor transport affinity for folic acid and thus, this oxidized folate cannot be used for in the culture medium for selection. However, folic acid can be processed by the folate receptor. Furthermore, the folate-receptor based selection system is a unidirectional folate uptake system wherein RFC is a bi-directional folate transporter that exhibits equally potent import and export of folates. Thus, the use of the folate receptor has several important advantages. However, it may also be used in combination with RFC as selectable marker.

Respective folate receptors can be introduced into the eukaryotic cell intended to produce a product of interest via the expression vector or combination of at least two expression vectors according to the present invention. Following the introduction of a polynucleotide encoding a folate receptor as first selectable marker (sm I) as well as the polynucleotide encoding a product of interest (like a polypeptide) and the polynucleotide encoding the second selectable marker (sm II), cells are grown in a selective medium containing limiting concentrations of folates. The lower the concentration of folate in the culture medium the more stringent are the applied selection conditions. Preferably, when the first selectable marker (sm I) is or comprises a folate receptor, the second selectable marker (sm II) is a catalytic polypeptide processing a substrate which is either a folate and/or a subsequent product obtained from a folate. Hence, cells that over express the introduced folate receptor can take up sufficient amounts of folates to sustain cell growth, DNA replication and thus cellular proliferation. This effect is further enhanced due to the fact that the activity of the second selectable marker (sm II) is dependent/influenced by the activity of the first selectable marker (sm I), here the transporter activity of the folate receptor (see above). This has the effect that only those cells survive which strongly overexpress the introduced selectable markers (sm I) and (sm II) and accordingly, overexpress the product of interest. This approach requires depending on the chosen embodiment no prior deletion of an endogenous folate receptor (FR) gene, even though this constitutes a possible embodiment.

The folate receptor introduced into the eukaryotic host cell by means of an expression vector utilized according to the present invention can be derived from any species as long as it will be functional within the present invention, i.e. compatible with the eukaryotic cell utilized. Preferably, a folate receptor derived from a mammalian species will be used, for example derived from a rodent, or, mostly preferred, a human folate receptor.

In general, the folate transporter, particularly the folate receptor introduced into the eukaryotic host cell and utilized as selection marker can be homologous or heterologous to an endogenous folate receptor of the host cell. If it is homologous it will be derived from the same species as the host cell, and may, for example, be identical to an endogenous folate receptor of the host cell. If it is heterologous, it will be derived from another species than the host cell, and may thus be different from an endogenous folate receptor of the host cell. Typically, the introduced folate transporter, preferably receptor utilized as selection marker will be heterologous to the host cell. For example a human-derived folate receptor may be used as selection marker for a rodent host cell, e.g. a CHO cell.

According to one embodiment, the folate receptor is a functional membrane-bound folate receptor. Said receptor may be a functional membrane-bound receptor capable of unidirectional import or uptake of a folate or derivative thereof into a eukaryotic cell. The membrane bound folate receptor can be derived from any species as is outlined above.

The functional membrane-bound folate receptor used as first selectable marker (sm I), can be selected from the group consisting of a folate receptor alpha, a folate receptor beta, a folate receptor gamma, a folate receptor having or comprising the amino acid sequence of SEQ. ID. NO. 1, 2 or 3 and functional variants of the foregoing. Preferably, it is a human folic receptor alpha or a functional variant thereof.

A functional variant comprises a derivative of a folate receptor which is functional in a physiological manner, i.e. capable of folate uptake by the host cell (which is in particular a eukaryotic and preferably a mammalian host cell) and contributes to the cell's viability via the cell's folate metabolism. For example, a variant form of the folate receptor may comprise one or more amino acid mutation(s), like a substitution, deletion and/or addition of one or more amino acids. Also encompassed by said term variant are fusion proteins comprising a respective folate receptor.

Preferably, the folate receptor is a human folate receptor alpha, a human folate receptor beta, or a functional variant thereof. Most preferred is a human folate receptor alpha having or comprising the following amino acid sequence (SEQ. ID. NO. 1, 1-letter code, shown in direction from N-terminus to C-terminus):

MAQRMTTQLLLLLVWVAVVGEAQTRIAWARTELLNVCMNAKHHKEKPGPE

DKLHEQCRPWRKNACCSTNTSQEAHKDVSYLYRFNWNHCGEMAPACKRHF

IQDTCLYECSPNLGPWIQQVDQSWRKERVLNVPLCKEDCEQWWEDCRTSY

TCKSNWHKGWNWTSGFNKCAVGAACQPFHFYFPTPTVLCNEIWTHSYKVS

NYSRGSGRCIQMWFDPAQGNPNEEVARFYAAAMSGAGPWAAWPFLLSLAL

MLLWLLS

Another preferred embodiment relates to a human folate receptor beta having or comprising the following amino acid sequence (SEQ. ID. NO. 2, 1-letter code, shown in direction from N-terminus to C-terminus):

MVWKWMPLLLLLVCVATMCSAQDRTDLLNVCMDAKHHKTKPGPEDKLHDQ

CSPWKKNACCTASTSQELHKDTSRLYNFNWDHCGKMEPACKRHFIQDTCL

YECSPNLGPWIQQVNQTWRKERFLDVPLCKEDCQRWWEDCHTSHTCKSNW

HRGWDWTSGVNKCPAGALCRTFESYFPTPAALCEGLWSHSYKVSNYSRGS

GRCIQMWFDSAQGNPNEEVARFYAAAMHVNAGEMLHGTGGLLLSLALMLQ

LWLLG

In an alternative, a folate receptor is used as first selectable marker (sm I) which is naturally not membrane-bound. Such a non-membrane bound receptor can be altered in order to become membrane-bound. For example a membrane anchor can be provided and/or said folate receptor can be expressed as a fusion protein comprising the non membrane-bound folate receptor and a transmembrane region of another polypeptide. Likewise, other variants can be used which would be readily available for a person skilled in the art. Preferred examples in this respect would be based on the soluble folate receptor gamma, preferably the human soluble folate receptor gamma. In a most preferred embodiment thereof, the human soluble folate receptor gamma would have/comprise the following amino acid sequence (SEQ. ID. NO. 3, 1-letter code, shown in direction from N-terminus to C-terminus):

MDMAWQMMQLLLLLALVTAAGSAQPRSARARTDLLNVCMNAKHHKTQPSPE

DELYGQCSPWKKNACCTASTSQELHKDTSRLYNFNWDHCGKMEPTCKRHF

IQDSCLYECSPNLGPWIRQVNQSWRKERILNVPLCKEDCERWWEDCRTSY

TCKSNWHKGWNWTSGINECPAGALCSTFESYFPTPAALCEGLWSHSFKVS

NYSRGSGRCIQMWFDSAQGNPNEEVAKFYAAAMNAGAPSRGIIDS

Said receptor may be mutated or otherwise genetically altered, derivatized or modified to form a functional membrane-bound folate receptor capable of folate uptake within the context of the present invention.

As becomes apparent from the above, the selectable marker(s) (sm I) and/or (sm II) can be or can comprise a catalytic polypeptide involved in nucleic acid synthesis and/or the folate metabolism. According to one embodiment, the first selectable marker (sm I) is or comprises a transporter incorporating a compound involved in and/or essential for nucleic acid synthesis into the host cell and the second selectable marker (sm II) is a catalytic polypeptide involved in nucleic acid synthesis e.g. the generation of nucleotides. Preferably, the second selectable marker (sm II) is a catalytic polypeptide, preferably an enzyme involved in nucleic acid synthesis, in particular the folate metabolism. This is particular useful, if the first selectable marker (sm I) transports folate into the host cell and is e.g. a folate receptor.

In the process of nucleic acid synthesis, the first enzyme, glycinamide ribonucleotide transformylase (GARTF), is involved in the formation of the imidazole ring of purines, whereas the more downstream reaction mediated by 5-aminoimidazole-4-carboxamide ribonucleotide transformylase (AICARTF) yields the purine intermediate inosine 5'-monophosphate (IMP). The latter serves as a key precursor for the regulated biosynthesis of AMP and GMP. Furthermore, 5,10-methylene-THF (5,10-$CH_2$-THF), is another important THF coenzyme which functions as a crucial cofactor for the enzyme thymidylate synthase (TS). TS catalyzes the formation of thymidine monophosphate (dTMP) from dUMP using 5,10-methylene-THF (5,10-CH$_2$-THF), thereby rendering dihydrofolic acid. Dihydrofolate reductase (DHFR) catalyzes the NADP-dependent reduction of dihydrofolic acid (DHF) to tetrahydrofolic acid (THF). THF is then interconverted to 10-formyl-THF and 5,10-methylene-THF which are used in the de novo biosynthesis of purines and thymidylate, respectively. This reaction is catalysed by the serine hydroxymethyltransferase (SHMT). DHF is accordingly the byproduct of the catalytic activity of thymidylate synthase (TS) which catalyzes the conversion of dUMP to dTMP in a 5,10-methylene-THF-dependent reaction. Thus, DHFR is crucial for the recycling of THF cofactors that are essential for the biosynthesis of purine and pyrimidine nucleotides that are necessary for DNA replication.

The described enzymes which are to a certain extent folate-dependent are key mediators of the de novo biosynthesis of purine and thymine nucleotides essential for DNA replication and are suitable as first selectable marker (sm I) and/or (sm II) as they are involved in the same metabolic process, namely nucleic acid synthesis.

According to one embodiment the second selectable marker (sm II) processes a substrate which is a folate, a derivative of folate and/or a product that can be obtained by the processing of folate such as DHF or THF or a functional variant or derivative of the foregoing. Respective substrates are important for the production of nucleic acids. Preferably, said second selectable marker (sm II) is or comprises the dihydrofolate reductase (DHFR) or an enzyme operating downstream/respectively in conjunction with DHFR such as TS and SHMT. This embodiment is particularly suitable if the selectable marker (sm I) is a folate transporter.

Several suitable DHFR enzymes and accordingly genes are known in the prior art that can be used in conjunction with the present invention. The DHFR may be a wildtype DHFR or a functional variant or derivative thereof. The term a "variant" or "derivative" include DHFR enzymes having one or more amino acid sequence exchanges (e.g. deletions, substitutions or additions) with respect to the amino acid sequence of the respective DHFR enzyme, fusion proteins comprising a DHFR enzyme or functional fragment thereof and DHFR enzymes which have been modified to provide an additional structure and/or function, as well as functional fragments of the foregoing, which still have at least one function of a DHFR enzyme. E.g. a DHFR enzyme may be used as selectable maker (sm II) that is e.g. more or less sensitive for antifolates such as MTX than the wildtype DHFR enzyme and/or the DHFR enzyme endogenously expressed by the host cell if expressed. The DHFR enzyme can be derived from any species as long as it will be functional within the present invention, i.e. compatible with the host cell utilised. E.g. a mutant mouse DHFR with a major resistance to MTX has been extensively used as a dominant selectable marker that markedly enhances the acquisition of high level MTX-resistance in transfectant cells. Preferably, a DHFR enzyme is used as selectable marker which is less susceptible to a DHFR inhibitor such as MTX than the DHFR enzyme endogenously expressed in a DHFR$^+$ (plus) host cell.

According to one embodiment, an intron or a fragment thereof is placed at the 3' end of the open reading frame of the DHFR gene. This has advantageous effects on the expression/amplification rate of the construct. The intron used in the DHFR expression cassette is leading to a smaller, non functional variant of the DHFR gene (Grillari et al., 2001, J. Biotechnol. 87, 59-65). Thereby the expression level of the DHFR gene is lowered and can thus further increase the stringency of the selection system. Accordingly, the host cell may comprise an introduced polynucleotide encoding a DHFR enzyme, said polynucleotide comprising an intron which is located 3' of the DHFR coding sequence. Alternative methods making use of an intron to reduce the expression level of the DHFR gene are described in EPO 724 639 and could also be used.

According to a preferred embodiment, the first selectable marker (sm I) is a folic acid receptor and the second selectable marker is a DHFR variant that is less sensitive to MTX than the wildtype DHFR enzyme and/or the DHFR enzyme endogenously expressed by the host cell. Said DHFR variant preferably also comprises an intron as is described above. A respective marker combination is particularly preferred in combination with DHFR$^+$ (plus) cells.

The teaching of the present invention can be carried out using different embodiments of expression vectors and/or combinations of at least two expression vectors as described herein. The polynucleotide encoding a product of interest or the insertion site for incorporating a respective polynucleotide, the polynucleotide encoding a first selectable marker (sm I) and/or the polynucleotide encoding a second selectable marker (sm II) and optionally further vector elements such as additional selectable markers can be located on the same or on separate expression vectors.

E.g. using an expression vector comprising at least all decisive elements described above, i.e. the polynucleotide encoding the product of interest (or an insertion site for incorporating a respective polynucleotide), the polynucleotide encoding the first selectable marker (sm I) and the polynucleotide encoding the second selectable marker (sm II), has the advantage that only one expression vector needs to be introduced into the host cell. Furthermore, in particular when establishing a stable expression line chances are higher that all elements are equally or at least expressed with a similar rate by the host cell as they would integrate together into the genome.

However, it is also possible and within the scope of the present invention to use a combination of at least two or three expression vectors for transfection, wherein the respective polynucleotides are located on different expression vectors. Said combination of expression vectors is then transfected into the host cell. When using a combination of at least two expression vectors, preferably a setting is used, wherein at least one polynucleotide encoding the product of interest (or the insertion site for introducing the polynucleotide of interest) and at least one of the selectable markers (sm I) or (sm II) is arranged on the same expression vector. This particularly, when the combination of expression vectors is used in order to establish a stable expression cell line, in order to ensure a tight coupling of the expression of the selectable marker ((sm I) and/or (sm II) to the expression of the product of interest. The other selectable marker (sm I) or (sm II) can be located on a separate expression vector of said expression vector combination. Said separate expression vector, which accordingly comprises the other selectable marker (sm I) or (sm II) may comprise an additional polynucleotide encoding a product of interest. A respective setting can e.g. be used for expressing immunoglobulin molecules. However, it is also within the teachings of the present invention that all polynucleotides (encoding the product of interest, (sm I) and (sm II)) are located on separate and thus individual expression vectors.

According to one embodiment, the expression vector according to the present invention comprises an insertion site for inserting the polynucleotide encoding a product of interest but not yet comprising the polynucleotide encoding the product of interest. A respective "empty" expression vector can be used for inserting the polynucleotide encoding the desired product of interest, thereby obtaining the ready to use expression vector that can be incorporated into the host cell in order to express the product of interest. The incorporation can be achieved by using appropriate cloning methods, for example by using restriction enzymes in order to insert the polynucleotide encoding the product of interest. For this purpose the expression vector may comprise e.g. a multiple cloning site (MCS) which can e.g. be used in all reading frames. A respective multiple cloning site as an example of an insertion site may be located within an expression cassette. A respective "empty" expression vector provides a useful tool for expressing different products of interests as the expression vector can be easily adapted to the intended use by inserting the polynucleotide encoding the desired product of interest.

The expression vector or the combination of at least two expression vectors can additionally comprise further vector elements. E.g. at least one additional polynucleotide encoding a further product of interest can be provided. This embodiment is particularly suitable for expressing immunoglobulin molecules. Further general vector elements that might be useful are known in the prior art and include but are not limited to origins of replication, further selection markers, promoters for expression in different host cells or in vitro expression.

The expression vector or combination of at least two expression vectors according to the present invention may comprise at least one polynucleotide encoding at least a functional fragment of the heavy chain of an immunoglobulin molecule and at least one polynucleotide encoding at least a functional fragment of the light chain of an immunoglobulin molecule.

Said polynucleotides may be located on the same or on different expression vectors in case a combination of at least two expression vectors is used. It is also within the scope of the present invention to use a combination of at least two expression vectors, wherein one expression vector comprises at least the polynucleotide encoding the first selectable marker (sm I) and at least a polynucleotide encoding at least a functional fragment of a light chain of an immunoglobulin molecule and/or a polynucleotide encoding a heavy chain of said immunoglobulin molecule and the other expression vector of said combination comprises at least the polynucleotide encoding the second selectable marker (sm II) and at least a polynucleotide encoding at least a functional fragment of a light chain of said immunoglobulin molecule and/or a polynucleotide encoding a heavy chain of said immunoglobulin molecule. A respective setting is also described in the examples. Upon expression of said polynucleotides in a host cell, a functional immunoglobulin molecule is obtained. The polynucleotide encoding at least a functional fragment of the heavy chain of an immunoglobulin molecule and the polynucleotide encoding at least a functional fragment of the light chain of an immunoglobulin molecule may be comprised in the same expression cassette or in different expression cassettes as is also described below.

The expression vector or combination of at least two expression vectors according to the present invention may additionally comprise one or more further polynucleotide(s) encoding one or more additional selectable marker(s). Said additional marker(s) may be involved in the same or a concerted metabolic process or pathway as the selectable markers (sm I) and (sm II). However, it may also be involved in a different metabolic pathway. In one embodiment of the present invention co-selection utilizing the system of the present invention together with one or more different selection system(s) (e.g. antibiotic resistance selection systems such as neo/G418) can be applied to further improve the performance. Besides further eukaryotic selectable markers which allow the selection of eukaryotic host cells, also prokaryotic selectable markers can be used. A "prokaryotic selectable marker" is a selectable marker allowing the selection in prokaryotic host cells under appropriate selection conditions. Examples of respective prokaryotic selectable markers are markers which provide a resistance to antibiotics such as e.g. ampicillin, kanamycin, tetracycline and/or chloramphenicol.

Vectors used for expressing products of interest usually contain transcriptional control elements suitable to drive transcription such as e.g. promoters, enhancers, polyadenylation signals, transcription pausing or termination signals as element of an expression cassette. If the desired product is a protein, suitable translational control elements are preferably included in the vector, such as e.g. 5' untranslated regions leading to 5' cap structures suitable for recruiting ribosomes and stop codons to terminate the translation process. In particular, the polynucleotide serving as the selectable marker genes as well as the polynucleotide encoding the product of interest can be transcribed under the control of transcription elements present in appropriate promoters. The resultant transcripts of the selectable marker genes and that of the product of interest harbour functional translation elements that facilitate substantial levels of protein expression (i.e. translation) and proper translation termination. A functional expression unit, capable of properly driving the expression of an incorporated polynucleotide is also referred to as an "expression cassette" herein. The polynucleotide(s) encoding the product of interest and the polynucleotides encoding the selectable markers sm (I) and (sm II) are preferably comprised in an expression cassette. Several embodiments are suitable, for example each of said polynucleotide(s) can be comprised in a different expression cassette. However, it is also within the scope of the present invention that at least two of the respective polynucleotides are comprised in one expression cassette.

Accordingly, the expression vector or combination of expression vectors according to the present invention may comprise at least one promoter and/or promoter/enhancer element as element of an expression cassette. Although the physical boundaries between these two control elements are not always clear, the term "promoter" usually refers to a site on the nucleic acid molecule to which an RNA polymerase and/or any associated factors binds and at which transcription is initiated. Enhancers potentiate promoter activity, temporally as well as spatially. Many promoters are transcriptionally active in a wide range of cell types. Promoters can be divided in two classes, those that function constitutively and those that are regulated by induction or derepression. Both are suitable in conjunction with the teachings of the present invention. Promoters used for high-level production of proteins in mammalian cells should be strong and preferably active in a wide range of cell types.

Strong constitutive promoters which drive expression in many cell types include but are not limited to the adenovirus major late promoter, the human cytomegalovirus immediate early promoter, the SV40 and Rous Sarcoma virus promoter, and the murine 3-phosphoglycerate kinase promoter, EF1a. Good results are achieved with the expression vector of the present invention when the promoter and/or enhancer is either obtained from CMV and/or SV40. The transcription promoters can be selected from the group consisting of an SV40 promoter, a CMV promoter, an EF1alpha promoter, a RSV promoter, a BROAD3 promoter, a murine rosa 26 promoter, a pCEFL promoter and a β-actin promoter.

A preferred embodiment relates to an expression vector according to the present invention, wherein the polynucleotide encoding a product of interest, the polynucleotide encoding a first selectable marker (sm I) and/or the polynucleotide encoding a second selectable marker (sm II) are under the control of distinct transcription promoters. In general, a promoter capable of promoting expression, in particular transcription, of the essential polynucleotides in a host cell, in particular a eukaryotic host cell will be suitable. The distinct transcription promoters driving the expression from the polynucleotides can be the same or different.

According to one embodiment, a stronger promoter and/or enhancer is used for driving the expression of the polynucleotide encoding the product of interest than for driving the expression of the polynucleotide encoding the first selectable marker (sm I) and/or (sm II). This arrangement has the effect that more transcript is generated for the product of interest than for the selectable markers. It is advantageous that the production of the product of interest is dominant over the production of the selectable markers, since the individual cell capacity for producing heterologous products is not unlimited and should thus be focused to the product of interest. Furthermore, the selection process only occurs at the initial stages of establishing an expression cell line, which then constantly produces the product of interest. Thus, it is advantageous to focus the resources of the cells to the expression/production of the product of interest. Furthermore, using a less strong promoter for expressing the selectable marker(s) (sm I) and/or (sm II) than the polypeptide of interest further increases the selection pressure.

According to one embodiment, the promoter driving the expression of the polynucleotide encoding the product of interest is a CMV promoter and the promoter driving the expression of the polynucleotide encoding the selectable marker (sm I) and/or (sm II) is a SV40 promoter. The CMV promoter is known to be one of the strongest promoters available for mammalian expression and leads to a very good expression rate. It is considered to give significantly more transcript than the SV40 promoter.

According to a further embodiment, the polynucleotide encoding the product of interest, the polynucleotide encoding a first selectable marker (sm I) and/or the polynucleotide encoding a second selectable marker (sm II) are under the control of the same transcription promoter. Suitable promoters are described above. In this embodiment, one long transcript is obtained from the respective expression cassette that is under the control of said transcription promoter. According to one embodiment, at least one IRES element is functionally located between the polynucleotide encoding a first selectable marker (sm I) and/or the polynucleotide encoding a second selectable marker (sm II). Thereby, it is ensured that separate translation products are obtained from said transcript.

The expression vector or combination of at least two expression vectors may comprise an appropriate transcription termination site as element of an expression cassette. This, as continued transcription from an upstream promoter through a second transcription unit may inhibit the function of the downstream promoter, a phenomenon known as promoter occlusion or transcriptional interference. This event has been described in both prokaryotes and eukaryotes. The proper placement of transcriptional termination signals between two transcription units can prevent promoter occlusion. Transcription termination sites are well characterized and their incorporation in expression vectors has been shown to have multiple beneficial effects on gene expression.

Preferably, the host cell used is a eukaryotic, in particular a mammalian host cell. Most eukaryotic nascent mRNAs possess a poly A tail at their 3' end which is added during a complex process that involves cleavage of the primary transcript and a coupled polyadenylation reaction. The polyA tail is advantageous for mRNA stability and transferability. Hence, the expression cassettes of the vector according to the present invention usually comprise a polyadenylation site. There are several efficient polyA signals that can be used in mammalian expression vectors, including those derived from bovine growth hormone (bgh), mouse beta-globin, the SV40 early transcription unit and the Herpes simplex virus thymidine kinase gene. However, also synthetic polyadenylation sites are known (see e.g. the pCl-neo expression vector of Promega which is based on Levitt el al, 1989, Genes Dev. 3, (7): 1019-1025). The polyadenylation site can be selected from the group consisting of SV40polyA site, such as the SV40 late and early poly-A site (see e.g. plasmid pSV2-DHFR as described in Subramani et al, 1981, Mol. Cell. Biol. 854-864), a synthetic polyA site (see e.g. the pCl-neo expression vector of Promega which is based on Levitt el al, 1989, Genes Dev. 3, (7): 1019-1025) and a bgh polyA site (bovine growth hormone).

Furthermore, an expression cassette comprising the polynucleotide encoding the product of interest, the polynucleotide encoding the first selectable marker (sm I) and/or the polynucleotide encoding the second selectable marker (sm II) may comprise at least one intron. This embodiment is particularly suitable when a eukaryotic, in particular a mammalian host cell is used for expression. Most genes from higher eukaryotes contain introns which are removed during RNA processing. Respective constructs are expressed more efficiently in transgenic systems than identical constructs lacking introns. Usually, introns are placed at the 5' end of the open reading frame but may also be placed at the 3' end. Accordingly, an intron may be comprised in the expression cassette(s) to increase the expression rate. Said intron may be located between the promoter and or promoter/enhancer element(s) and the 5' end of the open reading frame of the polynucleotide to be expressed. Several suitable introns are known in the state of the art that can be used in conjunction with the present invention.

According to one embodiment, the intron used in the expression cassettes for expressing the product of interest, is a synthetic intron such as the SIS or the RK intron. The RK intron is a strong synthetic intron which is preferably placed before the ATG start codon of the gene of interest. The RK intron consists of the intron donor splice site of the CMV promoter and the acceptor splice site of the mouse IgG Heavy chain variable region (see e.g. Eaton et al., 1986, Biochemistry 25, 8343-8347, Neuberger et al., 1983, EMBO J. 2(8), 1373-1378; it can be obtained from the pRK-5 vector (BD PharMingen)).

The expression vector or vector combination according to the present invention can be transfected into the host cell in its circular form. Supercoiled vector molecules usually will be converted into linear molecules within the nucleus due to the activity of endo- and exonucleases. However, linearization of the expression vector before transfection often improves the efficiency of a stable transfection. This also as the point of linearization may be controlled if the expression vector is linearized prior to transfection. Hence, according to one embodiment of the present invention the expression vector or combination of at least two expression vectors comprises at least one predefined restriction site, which can be used for linearization of the vector(s) prior to transfection. Intelligent placement of said linearization restriction site is advantageous, because said restriction site determines where the vector is opened/linearized and thus determines the order/arrangement of the expression cassettes when the construct is integrated into the genome of the eukaryotic, in particular mammalian cell. In case the vector is used as a standard expression vector intended e.g. as a tool for the expression of several different products/polypeptides, it is advantageous to provide a linearization restriction site comprising multiple recognition sites for enzymes having a low cutting frequency. The restriction enzymes chosen for linearization should preferably not cut within the expression cassettes for the product of interest, the selectable markers or other vector backbone sequences in order to ensure that the enzyme cuts only once for proper linearization of the vector. By providing a linearization restriction site comprising multiple recognition sites for restriction enzymes having a low cutting frequency, the user may chose a suitable restriction enzyme for linearization from the provided options in order to securely avoid restriction within the polynucleotide encoding the product of interest. However, as is outlined above, additional restriction sites may be mutated or a partial restriction digest could be performed. According to one embodiment, the linearization site is arranged such, that upon linearization, a polynucleotide encoding a eukaryotic amplifiable selectable marker is located 5' of the polynucleotide encoding the product of interest. This arrangement is advantageous for gene amplification. In case a prokaryotic selectable marker is additionally used, the polynucleotide encoding said marker is located 3' of the polynucleotide encoding the product of interest. This has the effect that the prokaryotic selection marker gene is 3' and thus "outside" of the "mammalian" parts of the linearized vector nucleic acid. This arrangement is favourable since prokaryotic genes are presumably not advantageous for eukaryotic and in particular mammalian expression as prokaryotic sequences may lead to increased methylation or other silencing effects in the mammalian cells.

The expression vector may comprise additional elements to allow the combination of the selection method according to the present invention with other selection systems known in the prior art. One established selection method known in the prior art is based on the use of flow cytometry, in particular fluorescence activated cell sorting (FACS). Selection methods employing flow cytometry have the advantage that large numbers of cells can be screened rapidly. In one selection method that is particularly useful to identify high producing cell clones, a portion of the product of interest e.g. an antibody is expressed as membrane bound fusion polypeptide. Thereby, a portion of the product is displayed as fusion polypeptide on the cell surface. As the amount of produced fusion polypeptide correlates with the overall expression rate, the host cells can be selected via flow cytometry based upon the amount of fusion polypeptide displayed on the cell surface. This allows the rapid selection of high producing host cells. It was found that the selection system according to the present invention can be advantageously combined with respective selection methods that are based on the use of flow cytometry. To allow efficient selection using FACS, preferably a special expression cassette is used for expressing the product of interest. Thus, according to one embodiment, the expression vector or the combination of at least two expression vectors according to the present invention comprises an expression cassette for expressing the polynucleotide encoding the product of interest that is designed such that a portion of the expressed product of interest comprises a transmembrane anchor. Several options exist to achieve that result.

According to one embodiment, said expression cassette comprises at least
  (a) the polynucleotide encoding the product of interest,
  (b) at least one stop codon downstream of the polynucleotide encoding the product of interest, and
  (c) a further polynucleotide downstream of the stop codon encoding a membrane anchor and/or a signal for a membrane anchor.

This design of the expression cassette has the effect that through translational read-through processes (the stop codon is "leaky") a portion of the product of interest is produced as a fusion polypeptide comprising a membrane anchor. As a result, this fusion polypeptide is displayed on the cell surface and cells displaying high levels of membrane-anchored fusion polypeptide can be selected by flow cytometry, preferably by FACS. Thereby, host cells are selected that have a high expression rate. Details and preferred embodiments of this stop codon based technology are described in WO2005/073375 and PCT/EP2009/006246. It is referred to this disclosure.

According to an alternative embodiment said expression cassette comprises at least
  (a) the polynucleotide encoding the product of interest,
  (b) an intron comprising a 5' splice donor site and a 3' splice acceptor site and comprising an in frame translational stop codon and a polyadenylation signal and
  (c) a polynucleotide downstream of said intron encoding a membrane anchor and/or a signal for a membrane anchor.

This design of the expression cassette has the effect that through transcription and transcript processing at least two different mature mRNAs (mRNA-POI) and (mRNA-POI-ANCHOR) are obtained from the expression cassette. Translation of the mRNA-POI results in the product of interest. Translation of the mRNA-POI-ANCHOR results in a fusion polypeptide comprising the product of interest and a membrane anchor. As a result, this fusion polypeptide is again displayed on the cell surface and cells displaying high levels of membrane-anchored fusion polypeptide can be selected by flow cytometry, preferably FACS. Thereby, host cells are selected that have a high expression rate. Details and preferred embodiments of this intron based technology are described in WO2007/131774. It is referred to this disclosure.

According to a preferred embodiment which is in particular useful for the expression of antibodies as product of interest, the membrane anchor is an immunoglobulin transmembrane anchor. Other suitable membrane anchors and preferred embodiments of an immunoglobulin transmembrane anchor are described in WO2007/131774, WO2005/073375 and PCT/EP2009/006246.

Also provided is a host cell comprising at least
  (a) an introduced polynucleotide encoding a product of interest;
  (b) an introduced polynucleotide encoding a first selectable marker (sm I);
  (c) an introduced polynucleotide encoding a second selectable marker (sm II), which differs from the first selectable marker (sm I);
wherein the activity of the selectable marker (sm I) or (sm II) is at least partially influenced by the activity of the other selectable marker.

According to one embodiment, the host cell comprises an expression vector or combination of at least two expression vectors as described in detail above and in the claims. We refer to the above disclosure.

Furthermore, the host cell may have at least one of the following characteristics:

The host cell is preferably a eukaryotic host cell. Said eukaryotic cell is, preferably, selected from the group consisting of a mammalian cell, an insect cell, a plant cell and a fungi cell. Fungi cells and plant cells can be prototrophic for folates (i.e. such cells can autonomously synthesize their own folates necessary for their cellular viability, i.e. cellular growth and proliferation). The present invention encompasses in particular such fungi and plant cells which are or may become auxotrophic for folates. This may be for example due to genetic manipulation, i.e. cells are now unable to synthesize sufficient amounts of folates necessary for their cellular viability. For example, the capacity of such fungi or plant cells to endogenously biosynthesize folates, e.g. via an appropriate metabolic pathway, can be inactivated, e.g. by gene disruption or gene silencing of appropriate target genes, or inhibition of key enzymes, etc. Preferably, the host cell is a mammalian cell. Said mammalian cell is preferably selected from the group consisting of a rodent cell, a human cell and a monkey cell. Particularly preferred is a rodent cell, which preferably is selected from the group consisting of a CHO cell, a BHK cell, a NSO cell, a mouse 3T3 fibroblast cell, and a SP2/0 cell. A most particularly preferred rodent cell is a CHO cell. Also preferred is a human cell, which, preferably, is selected from the group consisting of a HEK293 cell, a MCF-7 cell, a PerC6 cell, and a HeLa cell. Further preferred is a monkey cell, which, preferably, is selected from the group consisting of a COS-1, a COS-7 cell and a Vero cell.

The host cell and the incorporated selectable markers (sm I) and (sm II) shall be compatible, which means that the chosen combination of host cell and selectable markers (sm I) and (sm II) allows the selection of host cells expressing the respective markers under selective culture conditions. The expression of the selectable markers (sm I) and (sm II) shall provide a selective advantage under selective culture conditions. Thus, preferably a host cell is chosen, which is susceptible to selection by the selectable markers (sm I) and (sm II) under selective growth conditions. For example, in case a certain enzyme is used as selectable marker (sm I) and/or (sm II), the host cell may not express the respective enzyme endogenously or may at least express said enzyme not in sufficient amounts or with a sufficient activity in order to allow the cell to function/grow properly under selective culture conditions in the absence of a sufficient expression of the heterologous polynucleotides encoding the selectable markers (sm I) and (sm II). Thus, the host cell can only survive/proliferate with a sufficient rate, if the host cell expresses the introduced selectable markers and accordingly the polynucleotide encoding the product of interest with a sufficient yield to survive the selective growth conditions. The choice/design of suitable host cells depend on the chosen selectable markers (sm I) and (sm II). Suitable host cells are known in the prior art or could be generated by developing appropriate cell lines e.g. by genetic engineering (e.g. mutagenesis, gene knock-out; gene silencing and the like). These principles are well-known in the prior art and thus need no detailed explanation here.

E.g. host cells (e.g. CHO cells) that lack the DHFR gene (e.g. by targeted genomic deletion, also called DHFR⁻ host cells) can be used as recipients for the transfection of the DHFR gene as selectable marker gene in a medium that is free of nucleotides. However, it is also possible to use host cells that express DHFR endogenously (DHFR$^+$ (plus) host cells) when performing a DHFR selection if appropriate selective culture conditions are used. In this case, preferably a DHFR enzyme is used as selectable marker (sm II) which is less sensitive to MTX than the endogenous DHFR enzyme expressed by DHFR$^+$ (plus) host cell. After transfection with the heterologous polynucleotides, e.g. an expression vector according to the present invention comprising the DHFR gene e.g. as second selectable marker (sm II), the cells can be subjected to a gradual increase in the concentrations of inhibitors of DHFR. One example are antifolates such as MTX, which is a potent DHFR inhibitor (Kd=1 µM). The presence of the antifolate such as MTX in the medium forces the cells to produce increased levels of DHFR in order to survive. Upon multiple rounds of selection, the selectable marker DHFR frequently undergoes significant gene amplification in order to achieve that. The prior art must use rather high antifolate/MTX concentrations in order to achieve a sufficient gene amplification and accordingly, increase in the production of the product of interest. This is a disadvantage as antifolates are toxic and may alter the host cell. The novel approach of the present invention to combine two selectable markers (sm I and sm II) which are involved in the same or a concerted metabolic pathway (preferably the folate metabolism) has the advantage that the selection stringency is considerably increased already at low inhibitor (e.g. MTX) levels. Thus, less inhibitor and thus toxic agents are needed with the teachings of the present invention compared to the approaches of the prior art for providing very stringent selection conditions.

Suitable examples for selectable markers (sm I) and (sm II) as well as combinations thereof are described in detail above; we refer to the above disclosure.

The polynucleotide encoding a product of interest, the polynucleotide encoding a first selectable marker (sm I) and/or the polynucleotide encoding a second selectable marker (sm II) may be stably introduced into said host cell. The stable introduction respectively transfection is advantageous for establishing of expression cell lines and in particular for the large scale and accordingly industrial production of the product of interest.

The polynucleotide encoding a product of interest, the polynucleotide encoding a first selectable marker (sm I) and/or the polynucleotide encoding a second selectable marker (sm II) can be located on the same or on separate expression vectors comprised in said host cells. Details regarding these embodiments were described above; we refer to the above disclosure.

According to one embodiment, the cellular viability or proliferation rate of the used host cell may dependent on the uptake of a compound (such as e.g. folate) that is incorporated by the first selectable marker (sm I) into the host cell. As is outlined above, the first selectable marker (sm I) may encode a transporter polypeptide capable of importing a compound into said host. According to one embodiment described in detail above, the first selectable marker (sm I) imports at least one folate into the host cell and preferably, is a folate receptor as is described above. This embodiment works particularly well when using DHFR as second selectable marker (sm II). According to a preferred embodiment, the first selectable marker (sm I) is a folic acid receptor and the second selectable marker is a DHFR variant that is less sensitive to MTX than the wildtype DHFR enzyme. A respective marker combination is particularly preferred in combination with DHFR$^+$ (plus) cells. In this case, preferably a DHFR enzyme is used as selectable marker (sm II)

which is less sensitive to MTX than the endogenous DHFR enzyme expressed by DHFR$^+$ (plus) host cell. Details are described above and below.

According to one embodiment, the host cell is lacking the full activity of at least one endogenous functional membrane-bound folate receptor. Respective cell lines can be obtained through selection/screening processes or by genetic engineering techniques e.g. in order to generate knock-out cell lines. Thus, also a host cell is provided, wherein the endogenous unidirectional functional folate transport system, for example comprising at least one endogenous functional membrane-bound folate receptor, is lacking full activity, i.e. is attenuated. Such attenuation can be provided for example by any type of mutagenesis of the endogenous folate transport system in question, e.g. the endogenous functional membrane-bound folate receptor, for example by point mutation, gene disruption, and the like. The attenuation can be a partial or complete. In the latter case the eukaryotic cell according to the present invention does not comprise an endogenous functional unidirectional functional folate transport system, e.g. an endogenous functional membrane-bound folate receptor.

According to one embodiment, the host cell according to the present invention comprises at least one endogenous functional unidirectional functional folate transport system in addition to the heterologous functional membrane-bound folate receptor introduced into said host cell e.g. via the expression vector described above, in particular one or more endogenous functional membrane-bound folate receptor(s). It is an advantage of the present invention that the selection system described herein can be utilized even in the presence of such endogenous unidirectional functional folate transport system, i.e. where such endogenous system is retained. This, as the use of the respective host cells for the subsequent production of the product of interest under non-selective conditions is easier to handle if the endogenous system is retained and thus functional.

Accordingly, a further preferred embodiment relates to a host cell of the present invention, comprising at least one endogenous unidirectional functional folate transport system, wherein such endogenous unidirectional functional folate transport system preferably comprises at least one endogenous functional membrane-bound folate receptor. In a preferred embodiment thereof, the endogenous functional membrane-bound folate receptor is selected from the group consisting of the folate receptor alpha and the folate receptor beta.

Further suitable combinations are the choice of a folate receptor as first selectable marker (sm I) combined with a mutant DHFR as second selectable marker (sm II) which is less susceptible to a DHFR inhibitor such as MTX than the DHFR enzyme endogenously expressed in a DHFR$^+$ (plus) host cell. Said host cell may also be RFC$^+$ (plus) as is outlined above.

Also provided is a method for producing a host cell as described above, comprising the step of introducing into said host cell at least
  (a) a polynucleotide encoding a product of interest;
  (b) a polynucleotide encoding a first selectable marker (sm I);
  (c) a polynucleotide encoding a second selectable marker (sm II), which differs from the first selectable marker (sm I);
wherein the activity of the selectable marker (sm I) or (sm II) is at least partially influenced by the activity of the other selectable marker.

There are several appropriate methods known in the prior art for introducing polynucleotides and expression vectors into a host cells, including eukaryotic such as mammalian host cells. Respective methods include but are not limited to calcium phosphate transfection, electroporation, lipofection, biolistic- and polymer-mediated genes transfer. Besides traditional random integration based methods also recombination mediated approaches can be used to transfer the polynucleotide encoding the product of interest, the polynucleotides encoding a first selectable marker (sm I) and/or the polynucleotide encoding a second selectable marker (sm II) into the host cell genome. Such recombination methods may include use of site specific recombinases like Cre, Flp or ΦC31 (see e.g. Oumard et al, Cytotechnology (2006) 50: 93-108) which can mediate directed insertion of transgenes. Alternatively, the mechanism of homologous recombination might be used to insert said polynucleotides (reviewed in Sorrell et al, Biotechnology Advances 23 (2005) 431-469). Recombination based gene insertion allows to minimize the number of elements to be included in the heterologous nucleic acid that is transferred/introduced to the host cell. For example, an insertion locus might be used that already provides promoter and poly-A site (exogenous or endogenous) such that only the remaining elements (e.g. the polynucleotide encoding the product of interest, the polynucleotide encoding a first selectable marker (sm I) and/or the polynucleotide encoding a second selectable marker (sm II)) needs to be transferred/transfected to the host cell. Embodiments of a suitable expression vector or combination of expression vectors according to the present invention as well as suitable host cells are described in detail above; we refer to the above disclosure.

Polynucleotides encoding suitable selectable markers (sm I) and (sm II) as well as combinations thereof are described in detail above; we refer to the above disclosure. According to one embodiment, an expression vector or a combination of expression vectors according to the present invention is introduced into the host cell. The expression vector and a combination of expression vectors is described in detail above and in the claims.

Also provided is a method for selecting at least one host cell capable of expressing a product of interest, comprising
  (a) providing a plurality of host cells, comprising at least
    (i) an introduced polynucleotide encoding a product of interest;
    (ii) an introduced polynucleotide encoding a first selectable marker (sm I);
    (iii) an introduced polynucleotide encoding a second selectable marker (sm II); which differs form the first selectable marker (sm I);
    wherein the activity of the selectable marker (sm I) or (sm II) is at least partially influenced by the activity of the other selectable marker;
  (b) culturing said plurality of host cells under conditions selective for the selectable markers (sm I) and (sm II), thereby obtaining a host cell expressing the product of interest.

The term "selecting" or "selection" as used herein, in particular refers to a process of using a selectable marker and selective culturing conditions to select and accordingly obtain host cells that have incorporated the vector or vector combination according to the present invention. Thereby, successfully transfected host cells can be isolated and/or enriched from the population of transfected host cells.

Host cells that have not successfully incorporated the vector or vector combination according to the present invention preferably die or are impaired in growth under the selective culture conditions compared to host cells that have successfully incorporated the vector or vector combination according to the present invention. During selection, host cells which have successfully incorporated the vector or vector combination according to the present invention can be enriched as pool from the population of transfected host cells. Also individual host cells can be isolated from the population of transfected host cells during selection (e.g. by clonal selection). Suitable embodiments of selection procedures in order to obtain successfully transfected host cells (e.g. by FACS sorting or limited dilution) are well known in the prior art and accordingly, need no detailed description.

Suitable host cells and specific embodiments in particular regarding the choice of the selection markers (sm I) and (sm II) and combinations thereof are described in detail above. We refer to the above disclosure.

Depending on the used host cells and accordingly the chosen selection markers (sm I) and (sm II), the growth conditions are adapted in order to exert a selection pressure on the host cell. E.g. the selective culture medium may comprise suitable inhibitors for the catalytic polypeptides chosen as selectable markers (sm I) and/or (sm II). E.g. antifolates such as MTX can be used in order to inhibit the activity of DHFR when DHFR is used as selectable marker (sm II). Depending on the used concentration of said inhibitor in the culture medium (which may also be increased gradually), the stringency of the selection conditions is increased. Furthermore, in order to keep up the selection pressure, the culture medium should not comprise sufficient amounts of metabolites that allow to bypass the activity of the selection markers (sm I) and/or (sm II). E.g. if DHFR is used as selectable marker (sm II) it is advantageous that the selective culture medium does not comprise relevant nucleotides. In general metabolites interfering with said selection strategy shall be controlled, e.g. avoided.

Furthermore, in case the first selectable marker (sm I) is a transporter polypeptide, the selective culture medium should comprise a limiting concentration of said compounds essential for cell growth that are imported by the first selectable marker (sm I), e.g. folates in case the first selectable marker (sm I) transports folate into the host cell. The principles of choosing such selective conditions are known in the state of the art and can also be determined experimentally and thus need no detailed description. Suitable concentrations for folates and antifolates in particular suitable for fast growing suspension cells are also described herein.

The selection condition for the selectable markers (sm I) and (sm II) can be applied simultaneously. This increases the selective pressure and allows a faster selection procedure by sparing one selection step when optimal conditions are used. This reduces the time for obtaining suitable cell lines. E.g. for the selectable marker combination folate receptor/DHFR a growth medium can be used which comprises reduced amounts of folates and which comprises an inhibitor of DHFR. Suitable inhibitors are antifolates such as e.g. MTX.

In case a further selectable marker is used in addition to (sm I) and (sm II) the selective conditions for said selectable marker can be applied prior to (e.g. in a pre-selection step) or simultaneously with applying the selective conditions for the selectable markers (sm I) and/or (sm II). E.g. in case the neomycin phosphotransferase gene (neo) is used as additional selectable marker, the cells can be grown first in a medium e.g. containing G418 in order to select cells that have incorporated the expression vector or the combination of at least two expression vectors according to the present invention. This first medium can also already be selective for at least one of the selectable markers (sm I) or (sm II). Afterwards, the selective conditions for the selectable marker (sm I) and/or (sm II) are applied. This procedure is particularly useful in case one of the selectable markers (sm I) and/or (sm II) is an amplifiable selectable marker.

As is outlined above, preferably, (sm I) is a folate transporter, in particular a folate receptor, and accordingly, one embodiment of the present invention is based on the limited availability of a folate in the cell culture medium. The system will be widely applicable, and in particular to a eukaryotic cell which cellular viability depends upon the uptake of a folate. This embodiment can be used for the accelerated selection, screening and establishment of host cells, in particular eukaryotic, for example mammalian, cell clones that preferably stably overexpress high levels of recombinant products. Even more, and in contrast to other known selection systems, there is no essential need (although this is sometimes feasible) for modified cells, provided e.g. by mutating or knocking out endogenous gene(s). Since e.g. FR alpha displays a higher affinity for FA ($K_D$=0.1 nM) than, for example, RFC for leucovorin (Kt=1 µM), and transports folic acid into cells via a unidirectional pathway the present invention provides for the use of FR alpha and other folate receptors as a markedly improved dominant metabolic selectable marker, in particular, via gradual folate (e.g. folic acid) deprivation from the growth medium. This folate-based selection is an excellent strategy that is well-suited for the accelerated, stable and high level over-expression of target proteins in cultured mammalian cells.

The strategy of the present invention to use two to a certain degree interdependent selectable markers (sm I) and (sm II) that are preferably involved in a common or concerted metabolic process or pathway has the advantage that a very high stringency is obtained due to the additive/synergistic effects of the selection conditions targeting one metabolic pathway. Thus, the productivity of the cell population surviving selection is remarkably increased. The examples have shown that the host cells obtained after the selection method produce the product of interest with a high yield. Also the average productivity of the individual host cells is increased. Thus, chances are improved to find high producer clones with lower screening efforts. Thus, the selection system according to the present invention is superior to selection systems used in the prior art. In particular for the preferred combination of the use of a folate receptor in conjunction with a DHFR enzyme as selectable markers (sm I) and (sm II) host cells are obtained, which have a higher productivity compared to the use of the respective selectable markers alone. Thus, due to the higher stringency of the selection conditions, the selection procedure is optimized.

The selection method according to the present invention can also be performed quicker and more efficiently than conventional selection strategies known in the prior art, as the selection for the selectable markers (sm I) and (sm II) can be performed in one selection step, if optimal cell culture conditions are used.

The method may additionally comprise a step of
(c) selecting at least one host cell which expresses the product of interest with the desired yield.

Cells obtained as a result of the stringent screening/selection procedure of the present invention will generally be isolated and may be enriched from non-selected cells of the original cell population. They can be isolated and cultured as individual cells. It is, however, also possible to use an enriched population. The obtained host cells can also be used in one or more additional rounds of selection, optionally for additional qualitative or quantitative analysis, or can be used e. g. in development of a cell line for protein production. According to one embodiment, an enriched population of producing host cells selected as described above is directly used as population for the production of the polypeptide of interest with a good yield.

Preferably, a host cell is selected which stably expresses the product of interest. The advantages of a stable transfection/expression are described in detail above. We refer to the above disclosure.

In a most preferred embodiment of the method for selection, the plurality of host cells comprise host cells according to the present invention, i.e. as disclosed herein. We refer to the above detailed disclosure in particular on suitable selectable markers (sm I) and (sm II) and combinations thereof.

Further preferred embodiments in particular with respect to the host cells and the expression vector, respectively combination of expression vectors are described in detail above. We refer to the above disclosure.

Preferably, the first selectable marker (sm I) is a transporter/receptor that is capable of transporting folate into the host cell. This embodiment of the selection system according to the present invention does not require a genomic deletion or attenuation of the endogenous folate receptor alpha, beta or gamma genes prior to transfection and thus can be applied to any recipient cell even when some endogenous folate receptor gene expression is present (see above). This key advantage is based upon the fact that following folate receptor alpha transfection, cells can be exposed to an abrupt and severe deprivation of folates (e.g. folic acid) from the growth medium. Consequently, only transfectant cells which express significant amounts of the folate receptor alpha selectable marker can transport sufficient folate to sustain DNA replication and cellular proliferation. This occurs in the absence of any significant elevation in the expression of the endogenous folate receptor alpha gene. Furthermore, this embodiment of the selection system according to the present invention does not suffer from the loss of stringency of selection due to alleviation of the selective pressure via increased expression of alternative routes of folate uptake including increased expression of the endogenous RFC. This important advantage is due to the fact that whereas folate receptor alpha has an outstanding affinity for folic acid (Kd=0.1 nM), the RFC displays an extremely poor affinity for folic acid (Km=0.2-0.4 mM).

When (sm II) is DHFR or another enzyme of the nucleic acid synthesis pathway or specifically of the folate metabolism, the selective culture medium contains additionally an inhibitor of a respective enzyme, e.g. antifolates such as e.g. MTX in order to provide selective conditions.

The selective culture medium that is used in at least one selection step may comprise one or more types of folate. The folate comprised in the selective culture medium in a limiting concentration is capable of being taken up into and being processed by the host cell. Folates and in particular derivatives of folate which would not be processed by the host cell would not contribute to the selection pressure and accordingly would not contribute to the limiting concentration. The selective culture medium may have one or more of the following features:

(a) it comprises a limiting concentration of folate, preferably in a concentration of about 500 nM or less, about 250 nM or less, about 150 nM or less, about 100 nM or less, about 75 nM or less, about 50 nM or less, about 25 nM or less, about 15 nM or less, about 10 nM or less, about 5 nM or less or up to about 2.5 nM and wherein said folate is preferably folic acid; and/or (b) it comprises folic acid in a concentration of about 500 nM or less, about 250 nM or less, about 150 nM or less, about 100 nM or less, about 75 nM or less and preferably about 50 nM or less; and/or
(c) it comprises a DHFR inhibitor; and/or
(d) it comprises an antifolate; and/or
(e) it comprises an antifolate in a concentration of about 500 nM or less, about 350 nM or less, about 200 nM or less, preferably about 150 nM or less; and/or
(f) it comprises MTX as an antifolate; and/or
(g) it comprises MTX in a concentration of about 350 nM or less, 200 nM or less, preferably about 150 nM or less; and/or
(h) it comprises folic acid in a concentration of up to 100 nM, preferably up to 50 nM, and an equimolar concentration up to 20-fold of an antifolate.

Preferred concentrations of folate and in particular folic acid are selected from:
(a) about 500 nM-100 pM;
(b) about 250 nM-1 nM; preferably about 250 nM-2.5 nM or about 250 nM-5 or 10 nM;
(c) about 150 nM-1 nM; preferably about 150 nM-2.5 nM or about 150 nM-5 or 10 nM;
(d) about 100 nM-1 nM; preferably about 100 nM-2.5 nM or about 100 nM-5 or 10 nM;
(e) about 75 nM-1 nM, preferably about 75 nM-2.5 nM or about 75 nM-5 or 10 nM;
(f) about 50 nM-1 nM; preferably about 50 nM-2.5 nM or about 50 nM-5 or 10 nM;
(g) about 50 nM-12.5 nM; and
(h) about 25 nM-2.5 nM or about 25 nM-5 nM.

Preferred concentrations of antifolate and in particular MTX are selected from:
(a) about 500 nM-5 nM;
(b) about 350 nM-5 nM;
(c) about 200 nM-5 nM;
(d) about 100 nM-10 nM;
(e) about 50 nM-10 nM; and
(f) about 50 nM.

The preferred concentrations and concentration ranges of folate and antifolate described above can be combined with each other. In one embodiment, a folate concentration of about 12.5 nM-50 nM is used in combination with an antifolate concentration of 10 nM-100 nM. As described, preferably folic acid is used as folate and MTX as antifolate.

Furthermore, it was also found that the used folate and antifolate concentrations can influence each other. Thus, besides the absolute concentration of folates and antifolates, also the ratio can be a factor for providing suitable selection conditions. The concentration of antifolates (preferably MTX), can be up to about 20-fold of the folate (preferably folic acid) concentration. The antifolate (preferably MTX) concentration may be about 10-fold of the folate (preferably folic acid) concentration. Preferably, the selective culture medium comprises a folate and an antifolate in a concentration ratio of 1:10 to 10:1, preferably in a concentration ratio of 1:5 to 5:1. Very good results are obtained if approximately equimolar concentrations of folate and antifolate are used. As is shown by the examples, these ratios provide very suitable selective culture conditions to obtain high producing host cells. The selective culture medium described above also constitutes an individual element of the present invention as the present invention also provides a respective selective culture media suitable for selecting host cells according to the method of the present invention.

The concentrations described above are particularly suitable for fast growing suspension cells, which is a preferred phenotype for commercial production cell lines. However, different cell lines may have different folic acid consumption properties. Furthermore, the limiting concentrations may vary depending on the used folate, respectively antifolate. Therefore, the limiting concentrations of folate, in particular folic acid and antifolate, in particular MTX as well as the suitable folic acid to MTX ratios may differ depending on the chosen host cells and folate, respectively antifolate. Suitable concentrations, however, can easily be determined experimentally by the skilled person.

According to one embodiment, the host cells are pre-cultured in a folate free culture medium or in a culture medium comprising a limiting concentration of folate prior to transfection and/or selection. Suitable limiting concentrations of folate are described above. Preferably, said culture medium for pre-culturing the host cells comprises folate, in particular folic acid in a concentration of 50 nM or less.

As is outlined above, the selection method according to the present invention can be combined with flow cytometry based selection methods known in the prior art. Thus, according to one embodiment, a selection step involving flow cytometry is performed after the host cells were selected according to the method of the present invention in order to select host cells which express the product of interest with a high yield. For this purpose, preferably at least a portion of the product of interest is expressed as a membrane anchored fusion polypeptide that is displayed on the cell surface of the host cell. Based on the amount of displayed fusion polypeptide, host cells can be selected using flow cytometry, preferably using FACS, which express the product of interest with high yield.

According to a preferred embodiment, the polynucleotide of interest is thus expressed from
a) an expression cassette which comprises at least
   aa) the polynucleotide encoding the product of interest,
   bb) at least one stop codon downstream of the polynucleotide encoding the product of interest, and
   cc) a polynucleotide downstream of the stop codon encoding a membrane anchor and/or a signal for a membrane anchor;
   or
b) an expression cassette which comprises at least
   aa) the polynucleotide encoding the product of interest,
   bb) an intron comprising a 5' splice donor site and a 3' splice acceptor site and comprising an in frame translational stop codon and a polyadenylation signal and
   cc) a polynucleotide downstream of said intron encoding a membrane anchor and/or a signal for a membrane anchor.

Details regarding the design of these expression cassettes were discussed above. It is referred to the respective disclosure. For selection, the host cells are cultivated to allow the expression of the product of interest such that at least a portion of the product of interest is expressed as a fusion polypeptide comprising the membrane anchor, wherein said fusion polypeptide is being displayed on the surface of said host cell and wherein at least one host cell is selected based upon the amount of the fusion polypeptide displayed on the cell surface. As is discussed above, the host cells are preferably selected using flow cytometry, in particular FACS. As is shown in the examples, the combination of the selection method according to the present invention with a respective flow cytometry based selection approach is very advantageous and host cells are identified that have very good expression rates.

According to one embodiment, the present invention also provides a selective culture medium comprising folate in a limiting concentration and an antifolate. As is outlined above, the folate comprised in the selective culture medium in a limiting concentration is capable of being taken up into and being processed by the host cell. Folates and in particular derivatives of folate which would not be processed by the host cell would not contribute to the selection pressure and accordingly would not contribute to the limiting concentration. Said selective culture medium preferably has one or more of the characteristics described above for the selective culture medium used in conjunction with the described selection method of the present invention, in particular with respect to the concentration of the folate and antifolate comprised in the medium and preferred embodiments. Also the advantages were outlined in detail above. It is referred to the above disclosure which also applies here. Said selective culture medium can be used in conjunction with the selection system of the present invention.

Also provided is a process for producing a product of interest, comprising the step of culturing a host cell according to the present invention and/or a host cell selected according to the teachings of the present invention under conditions that allow for the expression of the product of interest.

Using the host cells according to the present invention for producing a product of interest, in particular a polypeptide has the advantage that the product of interest can be produced with a very high yield. This particularly, when performing the selection method according to the present invention for selecting appropriate host cells for expression. Thus, the present invention provides an improved method for producing a polypeptide of interest. Suitable host cells are described above; we refer to the above disclosure.

The expressed product of interest may be obtained by disrupting the host cells. The polypeptides may also be expressed, e.g. secreted into the culture medium and can be obtained therefrom. Also combinations of the respective methods are possible. Thereby, products, in particular polypeptides can be produced and obtained/isolated efficiently with high yield. The obtained product may also be subject to further processing steps such as e.g. purification and/or modification steps in order to produce the product of interest in the desired quality. According to one embodiment, said host cells are cultured under serum-free conditions.

The method for producing the product of interest may comprise at least one of the following steps:
    isolating the product of interest from said cell culture medium and/or from said host cell; and/or
    processing the isolated product of interest.

The product of interest, for example a polypeptide, produced in accordance with the invention may be recovered, further purified, isolated and/or modified by methods known in the art. For example, the product may be recovered from the nutrient medium by conventional procedures including, but not limited to, centrifugation, filtration, ultra-filtration, extraction or precipitation. Purification may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction.

The product of interest can be any biological product capable of being produced by transcription, translation or any other event of expression of the genetic information encoded by said polynucleotide. In this respect, the product will be an expression product. The product of interest may be selected from the group consisting of polypeptides and nucleic acids, in particular RNA. The product can be a pharmaceutically or therapeutically active compound, or a research tool to be utilized in assays and the like. In a particularly preferred embodiment, the product is a polypeptide, preferably a pharmaceutically or therapeutically active polypeptide, or a research tool to be utilized in diagnostic or other assays and the like. A polypeptide is accordingly not limited to any particular protein or group of proteins, but may on the contrary be any protein, of any size, function or origin, which one desires to select and/or express by the methods described herein. Accordingly, several different polypeptides of interest may be expressed/produced. The term polypeptide refers to a molecule comprising a polymer of amino acids linked together by a peptide bond(s). Polypeptides include polypeptides of any length, including proteins (e.g. having more than 50 amino acids) and peptides (e.g. 2-49 amino acids). Polypeptides include proteins and/or peptides of any activity or bioactivity, including e.g. bioactive polypeptides such as enzymatic proteins or peptides (e.g. proteases, kinases, phosphatases), receptor proteins or peptides, transporter proteins or peptides, bactericidal and/or endotoxin-binding proteins, structural proteins or peptides, immune polypeptides, toxins, antibiotics, hormones, growth factors, vaccines or the like. Said polypeptide may be selected from the group consisting of peptide hormones, interleukins, tissue plasminogen activators, cytokines, immunoglobulins, in particular antibodies or functional antibody fragments or variants thereof. In a most preferred embodiment the polypeptide is an immunoglobulin molecule or antibody, or a functional variant thereof, for example a chimeric, or a partly or totally humanized antibody. Such an antibody can be a diagnostic antibody, or a pharmaceutically or therapeutically active antibody.

Also provided is a product obtained by a method according to the present invention as defined above and in the claims. Said product is preferably a polypeptide, in particular an immunoglobulin molecule or a functional fragment thereof.

A further aspect of the present invention pertains to the use of a first selectable marker (sm I) in combination with a second selectable marker (sm II) which differs from the first selectable marker (sm I), wherein the activity of the selectable marker (sm I) or (sm II) are at least partially influenced by the activity of the other selectable marker, for selecting a host cell being capable of expressing a product of interest.

The first selectable marker (sm I) and/or the second selectable marker (sm II) may have at least one of the following characteristics:
(a) the first selectable marker (sm I) and/or the second selectable marker (sm II) are involved in a metabolic process or pathway selected from
 (aa) nucleic acid synthesis and/or polypeptide synthesis;
 (ab) nucleotide synthesis and/or amino acid synthesis; and
 (ac) the folate metabolism; and/or
(b) the first selectable marker (sm I) and/or the second selectable marker (sm II) is a catalytic polypeptide or a transporter polypeptide; and/or
(c) the second selectable marker (sm II) is a catalytic polypeptide processing
 (ca) a substrate which is a compound that is imported by the first selectable marker (sm I) into a host cell or a subsequent product obtained from said incorporated compound and/or
 (cb) a substrate which, or a precursor of which, is produced by the activity of the first selectable marker (sm I); and/or
(d) the first selectable marker (sm I) operates upstream of the second selectable marker (sm II); and/or
(e) the first selectable marker (sm I) is or comprises a transporter polypeptide importing a compound involved in and/or essential for cell viability and/or proliferation into a host cell; and/or
(f) the first selectable marker (sm I) transports/incorporates at least one folate into the host cell; and/or
(g) the first selectable marker (sm I) is or comprises a functional membrane-bound folate receptor; and/or
(h) the second selectable marker (sm II) is a catalytic polypeptide processing a substrate which is either a folate and/or a subsequent product obtained from a folate; and/or
(i) the first selectable marker (sm I) is a functional membrane-bound folate receptor which is or comprises a folate receptor having one or more of the following characteristics
 (ia) the folate receptor is selected from the group consisting of a folate receptor alpha, a folate receptor beta, a folate receptor gamma and functional variants of the foregoing, and/or
 (ib) the folate receptor is a human folate receptor or a functional variant thereof, and/or
 (ic) the folate receptor is a human folate receptor alpha or a functional variant thereof, and/or
 (id) the folate receptor is a folate receptor having or comprising the amino acid sequence of SEQ. ID. NO. 1, 2 or 3 or a functional variant of the foregoing; and/or
(j) the selectable marker(s) (sm I) and/or (sm II) is or comprises a catalytic polypeptide involved in nucleic acid synthesis and/or the folate metabolism, preferably DHFR or a functional variant or fragment thereof; and/or
(k) the first selectable marker (sm I) is or comprises a transporter polypeptide incorporating a compound involved in and/or essential for nucleic acid synthesis into a host cell and the second selectable marker (sm II) is a catalytic polypeptide involved in nucleic acid synthesis; and/or
(l) the first selectable marker (sm I) and/or the second selectable marker (sm II) is a eukaryotic selectable marker; and/or
(m) the first selectable marker (sm I) and/or the second selectable marker (sm II) is an amplifiable selectable marker.

Details, combinations and advantages of these embodiments are described above. We refer to the above disclosure. Particularly preferred is a combination of a folate transporter such as a folate receptor with DHFR or a functional variant or derivative thereof.

The full contents of the texts and documents as mentioned herein are incorporated herein by reference and thus form part of the present disclosure.

The following examples serve to illustrate the present invention without in any way limiting the scope thereof. In particular, the examples relate to preferred embodiments of the present invention.

EXAMPLES

In general, the suitable materials, such as reagents, are familiar to the skilled person, commercially available and can be used in accordance with the manufacturer's instructions. The examples are performed according to the described instructions.

1. Example 1—Selection

A co-transfection experiment in CHO cells is done using vectors having identical expression cassettes for the same protein of interest (monoclonal antibody) but different combinations of selectable markers. This experiment demonstrates that a combined selection of MTX and limiting folic acid concentrations in the cell culture medium allows the generation of cell populations highly overexpressing the product of interest, here an immunoglobulin molecule, and that the productivity of these populations is higher compared to strategies using DHFR or folic receptor alpha (FolR) as metabolic selectable marker alone.

1.1. Materials and Methods
1.1.1. Vector Construction:

VECTOR I contains a DHFR (mutant for dhfr+(plus) cell lines) expression cassette. Said plasmid vector (VECTOR I), suitable for expression in eukaryotic cells, in particular CHO cells, harbours:

(i) an expression cassette which comprises a polynucleotide encoding the heavy and an expression cassette encoding the light chain of a secreted recombinant human antibody of IgG1 type. Expression of the recombinant antibody is under control of a CMV promoter and a standard (SV40) polyadenylation signal;

(ii) a distinct expression cassette which comprises a polynucleotide encoding DHFR (a mutated form having a lower sensitivity for MTX) as selectable marker gene (sm II). Expression of the DHFR is under control of a SV40 promoter and a standard (SV40) polyadenylation signal.

The plasmid vector (VECTOR II) comprises a human folic acid receptor alpha as first selectable marker (sm I) instead of DHFR. Thus, both vectors contain a G418 resistance gene (neo) but different additional markers, namely DHFR or the human folic receptor alpha. VECTOR I and VECTOR II comprise the following major elements:

| Elements of VECTOR I | Elements of VECTOR II |
| --- | --- |
| CMV promoter/enhancer | CMV promoter/enhancer |
| RK-Intron | RK-Intron |
| Polynucleotide encoding the antibody light chain | Polynucleotide encoding the antibody light chain |
| SV40 Poly A site | SV40 Poly A site |
| CMV promoter/enhancer | CMV promoter/enhancer |
| RK-Intron | RK-Intron |
| Polynucleotide encoding the antibody heavy chain | Polynucleotide encoding the antibody heavy chain |
| SV40 Poly A site | SV40 Poly A site |
| SV40 enhancer/promoter | SV40 enhancer/promoter |
| Neomycin resistance gene | Neomycin resistance gene |
| Synthetic Poly A site | Synthetic Poly A site |
| An ampicillin resistance gene | An ampicillin resistance gene |
| SV40 promoter | SV40 promoter |
| Polynucleotide encoding DHFR (mutant) | huFolR |
| SV40 intron fragment | |
| SV40 Poly A site | SV40 Poly A site |

1.1.2. Transfection and Selection of CHO-Cells:

Cell cultivation, transfection and screening are carried out in shake flasks using suspension growing CHO cells in a conventional culture medium. In order to reduce intracellular folic acid reservoirs in the host cells and to prevent co-transfer of folic acid from the pre-culture medium to the selection medium, cells are passaged to folic acid free medium or medium with reduced folic acid content (e.g. 50 nM) prior to the transfection and selection.

Cells are co-transfected with VECTOR I and VECTOR II by electroporation. Depending on the cell viability, a first selection step is started 24-48 h after transfection by adding G418 and 10 nM folic acid containing selective medium to the cells. As soon as cells recovered to a viability of above 80%, a second selection step is applied by passaging the cells to G418 free medium containing 100 nM MTX and 10 nM folic acid. The folic acid concentration can be increased to 20 nM and subsequently to 100 nM if the cells do not recover under the more stringent conditions. Those pools where still no growth but increasing viabilities can be seen cells are transferred to culture medium containing 11.3 µM folic acid and no MTX. After this transfer, co-transfected cell populations that start to grow are expanded for further analysis.

1.1.3. Determination of Pool Productivity:

Productivity of the selected cell populations is analyzed after the first and final selection steps via overgrown shake flask batch cultures in medium containing 11.3 µM folic acid without G418 and MTX.

Batch cultures are seeded in shake flask 125 with 50 ml working volume and cultivated in a shaker cabinet (not humidified) at 150 rpm and 10% $CO_2$. Viability of cells have to be >90% when starting the assay. The seeding cell density is approximately $2\times10^5$ c/ml. Titer determination takes place at day 13. Antibody titers in the cell culture supernatant are determined by protein-A HPLC 13 days after starting the culture.

1.2. Results

To demonstrate the efficacy of a selection strategy using DHFR and FolR as selectable markers, a co-transfection of the vectors encoding DHFR (VECTOR I) and FolR (VECTOR II) and an identical monoclonal antibody is done. Both vectors also contain a G418 resistance gene (see above).

1.2.1. First Selection Step:

First, transfected cell populations are selected by adding G418 and reducing the folic acid concentration to 10 nM. This initial pre-selection step helps to kill untransfected cells and in parallel forces the cells to consume their intracellular folic acid reservoirs before the more stringent selection conditions are applied in the second selection step. Under these first selection conditions all transfected cell populations usually recover and the productivity is assessed as described in materials and methods. Transfected cells selected in G418 and 10 nM folic acid containing medium are analyzed in shake flask batch cultures. At day 13 of the culture, samples of the culture medium are taken and analyzed for antibody content by Protein-A HPLC. Table 1 summarizes the productivity results obtained in a respective example:

TABLE 1

Productivity of cell populations after the first selection step without MTX

| Pool Nr | Vector<br>VECTOR I (dhfr) and VECTOR II (FolR)<br>mg/L |
| --- | --- |
| 1 | 53 |
| 2 | 42 |
| 3 | 62 |
| 4 | 66 |
| 5 | 47 |

All cell populations produce antibody. Cells transfected with the FoIR vector (VECTOR II) in combination with DHFR vector (VECTOR I), respond with higher average productivities to the selection than conventional prior art methods (e.g. DHFR alone). The limited folic acid content in the culture medium promotes growth of cells overexpressing FoIR.

1.2.2. Second Selection Step:

To increase selection stringency, the next step is to remove G418 but to add 100 nM MTX to the culture medium and to keep folic acid concentration at 10 nM. Under these conditions, viability of the cells of all transfected populations dramatically drops and stays at low levels. In addition, no cell growth is usually detected. The selective pressure can be reduced by increasing the folic acid content first to 20 nM and then to 100 nM. In order to push growth of the selected populations for productivity assessment, recovered viable cells can be transferred to a medium without MTX and with 11.3 µM folic acid. One already partially recovered pool from the double transfection is kept separately and in medium containing 100 nM folic acid, while the other pools of each vector combination are combined to increase the cell density and thereby the chances of survival. The double transfected cells respond with fast growth, are further expanded and the productivity is analyzed. Tab. 2 shows the results:

TABLE 2

Productivity of cell populations after second selection step

| Pool Nr | Vector VECTOR I (dhfr) and VECTOR II (FoIR) mg/L |
|---|---|
| 1 | 1110 |
| 2-5 | 524 |

G418 and 10 nM folic acid selected cell populations are further selected by adding 100 nM MTX and a stepwise increase of the folic acid concentration. Finally, cells are transferred to MTX free and 11.3 µM folic acid containing medium and recovered populations are analyzed in shake flask batch cultures. At day 13 of the culture, samples of the culture medium are taken and analyzed for antibody content by Protein-A HPLC.

The productivity of the double transfected cell populations after this selection process is surprisingly high. Compared to the first selection step, antibody titers increased by approximately 20-fold in case of pool 1 reaching over 1 g/L and 10-fold in case of the combined pools 2-5. Also, in comparison to much more intensively optimized selection procedures using e.g. DHFR alone in combination with G418 as selectable markers, the productivities found after double selection are much higher with the vector combination according to the present invention. Previous experiments using a DHFR/G418 combination for the same antibody resulted in considerably lower pool titers.

Thus, the combined selection using DHFR and FoIR as selectable markers generates cells highly overexpressing a protein of interest. This combination is also superior to state of the art selection systems (e.g. DHFR/G418).

2. Example 2: Optimization of Selection Conditions 2.1. Transfection, Selection and Clone Characterisation
2.1.1. Transfection and Selection:

For optimization of selection conditions, additional combinations of folic acid and MTX concentrations are tested in two sequential selection steps. First, in medium containing 0.8 g/L G418, folic acid concentrations of 12.5 nM, 25 nM, 50 nM and 11.3 µM (reference) are combined with 2.5 nM, 5 nM, or 10 nM MTX or without MTX. Cell populations that recovered under these conditions in a second selection step are transferred to medium without G418 containing the same folic acid concentration but a 10-fold higher MTX concentration as in the first selection step. The reference cells are transferred to medium containing 500 nM MTX according to a DHFR selection standard protocol.

2.1.2. Cloning and Clone Characterisation

Cloning is performed by limiting dilution with the cells seeded in 96-well plates at a density of 0.5 cells per well. Subsequently, cells are expanded first to 24-well plates and then to shake flasks for productivity screening.

The productivity of clones is analyzed in batch and fed batch experiments using different formats. Initial screening is performed in 24-well plate batch assays by seeding cells into shaken 24-well plates. Antibody titers in the cell culture supernatant are determined by quantitative Protein A-HPLC 10 days after starting the culture. The highest producing clones are subsequently analyzed in shake flask models in batch and fed batch mode. Batch cultures in culture medium containing 11.3 µM folic acid are seeded into shake flasks (500 mL or 250 mL capacity) with 100 mL or 50 mL working volume and are cultivated in a shaker cabinet (not humidified) at 150 rpm, 36.5° C. and 10% $CO_2$. Viability of cells is >90% when starting the assay. The seeding cell density is $2\times10^5$ c/mL. Antibody titer, cell number and viability can be determined at defined culture time points. Fed batch experiments are done using the same conditions but with a starting cell density of $4\times10^5$ c/mL and with regular addition of feeds starting at viable cell densities above $7\times10^6$ c/mL. Clonal stability is evaluated by culturing the cells over a period of up to 19 weeks with productivity measurements using the shake flask batch model approximately every two weeks.

2.2. Results:
2.2.1. First Selection Step

Transfected cells are selected in a first selection step at folic acid concentrations ranging from 12.5 nM to 50 nM in combination with MTX concentrations from 2.5 nM to 10 nM. As a reference, also 11.3 µM folic acid (FA) is tested. The productivities obtained after the first selection step are summarized in table 3.

TABLE 3

Productivity of cells after the first selection step at different combinations of folic acid and MTX concentrations. All values are mg/L.

| Selection Marker | Folic Acid | no MTX | 2.5 nM MTX | 5 nM MTX | 10 nM MTX |
|---|---|---|---|---|---|
| Dhfr and FoIR | 12.5 nM FA | 16 | 19 | 27 | 333 |
|  | 25 nM FA | 18 | 16 | 24 | 70 |
|  | 50 nM FA | 12 | 18 | 13 | 887 |
| dhfr alone reference | 11.3 µM FA | 16 | 11 | 16 | 11 |

It is found that at the highest productivities are obtained after selection with 10 nM MTX. Cells co-transfected with VETCOR I and VECTOR II produce surprisingly high amounts of product (up to 887 mg/L). This is significantly more than the productivity of the cells transfected with DHFR alone (dhfr alone reference)

2.2.2. Second Selection Step:

A second selection step is applied to the recovered populations by transferring the cells to G418 free medium, keeping the folic acid concentration of the first selection step but increasing the MTX concentration 10-fold. Productivity is analyzed for cell population that recovered under these conditions. The results are summarized in table 4.

TABLE 4

Productivity of cells after the second selection step at different combinations of folic acid and MTX concentrations. All values are mg/L.

| Selection Marker | Folic Acid | 10 nM MTX | 25 nM MTX | 50 nM MTX | 100 nM MTX | 500 nM MTX |
|---|---|---|---|---|---|---|
| dhfr and FoIR | 12.5 nM FA | 457 | 869 | 1170 | 193 | nd |
|  | 25 nM FA | 624 | 967 | 842 | 907 | nd |
|  | 50 nM FA | 27 | 68 | 1540 | 1320 | nd |
| dhfr alone reference | 11.3 μM FA | Nd | nd | nd | nd | 31 |

Surprisingly, it is found that under appropriate selection conditions, cells transfected with VETCOR I and VECTOR II and accordingly a combination according to the present invention, have a much higher productivity (up to 1.5 g/L) compared to cells transfected with VECTOR I alone. This shows that the combination of DHFR and FoIR as selectable markers provides a highly increased selection stringency. Thus, the present invention provides a considerable improvement over the prior art.

2.2.3. Comparison of Clonal Productivity

Clones are generated by limiting dilution cloning from co-transfected pools after selection. The highest producing clones identified in 24 well plate screening are further expanded to shake flasks. Productivity is analysed in an overgrown shake flask batch assay and compared to the resultsts of the top clones obtained with the individual vectors in previous experiments.

TABLE 5

Productivity of top 5 clones from limiting dilution cloning in a shake flask batch model. All values are g/L of antibody at day 13-15 of the culture.

| Clone ranking | vector/selection | | |
|---|---|---|---|
|  | Dhfr | FoIR | dhfr/foIR |
| 1 | 0.52 | 1.10 | 1.46 |
| 2 | 0.51 | 1.09 | 1.44 |
| 3 | 0.50 | 0.99 | 1.44 |
| 4 | 0.49 | 0.85 | 1.41 |
| 5 | 0.47 | 0.85 | 1.40 |

The highest producing clones are obtained by co-transfecting vectors containing dhfr and foIR as selectabe markers and by selecting transfected cells under limiting folic acid concentrations plus MTX.

2.2.4. Analysis of Clonal Production Stability

Clonal production stability of the top 10 dhfr/foIR co-transfected and selected clones is determined over a period of 19 weeks starting from thawing the vials and the first productivity assessment at week 5 after thawing. Cells are cultured under selective conditions at 50 nM folic acid and 50 nM MTX. Productivity assay are performed with culture medium containing 11.3 μM folic acid.

TABLE 6

Clonal production stability of top 10 clones from limiting dilution cloning in a shake flask batch model. All values are mg/L of antibody at day 13-15 of the culture.

| Clone | Week 5 | Week 8 | Week 12 | Week 15 | Week 17 | Week 19 |
|---|---|---|---|---|---|---|
| 6A8 | 1070 | 1230 | 1040 | 924 | 980 | 987 |
| 7F2 | 1090 | 1140 | 1120 | 971 | 975 | 1060 |
| 7F7 | 1120 | 1240 | 1140 | 904 | 917 | 937 |
| 9C4 | 1110 | 1200 | 1030 | 769 | 560 | 573 |
| 9G12 | 1150 | 1240 | 1140 | 938 | 775 | 538 |
| 9H9 | 1100 | 1150 | 1130 | 969 | 1000 | 1040 |
| 10D3 | 1140 | 1130 | 1090 | 1020 | 1040 | 1090 |
| 10G10 | 1060 | 1180 | 1080 | 987 | 1080 | 1080 |
| 10H5 | 1100 | 1240 | 1170 | 1050 | 1140 | 1190 |
| 10H8 | 1050 | 1120 | 1140 | 1050 | 1020 | 1170 |

Eight of the ten clones analyzed show high production stability over 19 weeks and all ten clones show sufficient stability over 12 weeks.

3. Example 3—Selection Using a Combination Vector and FACS Sorting

3.1. Vector Construction:

A VECTOR III containing the selectable markers DHFR and FoIR on one backbone is generated which also allows further selection using FACS sorting. Said VECTOR III comprises an expression cassette for expressing the antibody heavy chain which comprises a "leaky" stop codon and an immunoglobulin transmembrane anchor. As is outlined above in the description, this design of the expression cassette has the effect (due to translational read through processes) that a portion of the antibodies are produced as fusion proteins which are anchored to the cell surface of the host cell. VECTOR III comprises the following major elements:

| Elements of VECTOR III |
|---|
| CMV promoter/enhancer |
| RK-Intron |
| Polynucleotide encoding the antibody light chain |
| SV40 Poly A site |
| CMV promoter/enhancer |
| RK-Intron |
| Polynucleotide encoding the antibody heavy chain |
| Stop codon (leaky) |
| Polynucleotide encoding the immunoglobulin transmembrane anchor including the cytoplasmatic domain |
| SV40 Poly A site |
| SV40 enhancer/promoter |
| Polynucleotide encoding the huFoIR |
| Synthetic Poly A site |
| An ampicillin resistance gene |
| SV40 promoter |
| Polynucleotide encoding DHFR (mutant) |
| SV40 intron fragment |
| SV40 Poly A site |

This DHFR/FoIR-FACS Vector (VECTOR III) is compared to a DHFR-FACS reference vector that contains the neo gene as second selectable marker (VECTOR IV). VECTOR IV comprises the following major elements:

| Elements of VECTOR IV |
| --- |
| CMV promoter/enhancer |
| RK-Intron |
| Polynucleotide encoding the antibody light chain |
| SV40 Poly A site |
| CMV promoter/enhancer |
| RK-Intron |
| Polynucleotide encoding the antibody heavy chain |
| Stop codon (leaky) |
| Polynucleotide encoding the immunoglobulin transmembrane anchor including the cytoplasmatic domain |
| SV40 Poly A site |
| SV40 enhancer/promoter |
| Neomycin resistance gene |
| Synthetic Poly A site |
| An ampicillin resistance gene |
| SV40 promoter |
| Polynucleotide encoding DHFR (mutant) |
| SV40 intron fragment |
| SV40 Poly A site |

Furthermore, for co-transfection experiments using two expression vectors and FACS sorting, VECTOR V is created which comprises no DHFR gene but the neo gene and the huFoIR. VECTOR V comprises the following major elements:

| Elements of VECTOR V |
| --- |
| CMV promoter/enhancer |
| RK-Intron |
| Polynucleotide encoding the antibody light chain |
| SV40 Poly A site |
| CMV promoter/enhancer |
| RK-Intron |
| Polynucleotide encoding the antibody heavy chain |
| Stop codon (leaky) |
| Polynucleotide encoding the immunoglobulin transmembrane anchor including the cytoplasmatic domain |
| SV40 Poly A site |
| SV40 enhancer/promoter |
| Neomycin resistance gene |
| Synthetic Poly A site |
| An ampicillin resistance gene |
| SV40 promoter |
| huFoIR |
| SV40 Poly A site |

3.2. Selection, Cloning and Clone Characterisation:

Cells transfected with the combination VECTOR III are selected in a medium containing 12.5 nM folic acid and 5 nM MTX. Cells transfected with the reference vector are selected in medium containing 12.5 nM folic acid, 5 nM MTX and 0.8 g/L G418. In a second selection step, applied after a FACS enrichment cycle the MTX concentration is increased to 50 nM while the folic acid concentration is kept constant and G418 is removed. The recovered cell populations (pools) are screened for productivity in shake flask batch cultures.

FACS Analysis, Enrichment and Cloning of Cells

Labelling of cells: 2×10E7 cells per transfected pool are centrifuged and washed with 5 mL of chilled PBS and resuspended in 1 mL of cold PBS. A suitable amount of FITC labelled anti-IgG antibody (supplier) is added to the cells and is incubated on ice for 30 minutes in the dark. Subsequently, cells are washed twice at room temperature with 5 mL PBS, resuspended in 1 mL PBS, filtrated and dispensed into a FACS tube for analysis, sorting and cloning. The cell sorting is performed with a FACSAria (Becton Dickinson) equipped with an Automatic Cell Deposition Unit (ACDU) using FACSDiva software. A low powered air-cooled and solid-state laser (Coherent® Sapphire™ solide state) tuned to 488 nm is used to excite fluorescein dyes bound to the secondary antibody. The relative FITC fluorescence intensity is measured on E detector through a 530/30 BP filter. Five percents of the highest FITC fluorescent cells are gated and sorted either in block or as single cells in 96 well plates.

Clones are generated either by limiting dilution from FACS enriched pools or by FACS cloning from enriched or non-enriched pools.

Determination of Antibody Production and Clonal Stability

The productivity of clones is analyzed in batch and fed batch experiments using different formats. Initial screening is performed in 24-well plate batch assays by seeding cells into shaken 24-well plates. Antibody titers in the cell culture supernatant are determined by quantitative Protein A-HPLC 10 days after starting the culture. The highest producing clones are subsequently analyzed in shake flask models in batch and fed batch mode. Batch cultures in culture medium containing 11.3 µM folic acid are seeded into shake flasks (500 mL or 250 mL capacity) with 100 mL or 50 mL working volume and are cultivated in a shaker cabinet (not humidified) at 150 rpm, 36.5° C. and 10% $CO_2$. Viability of cells should be >90% when starting the assay. The seeding cell density is $2 \times 10^5$ c/mL. Antibody titer, cell number and viability can be determined at defined culture time points. Fed batch experiments are done using the same conditions but with a starting cell density of $4 \times 10^5$ c/mL and with regular addition of feeds starting at viable cell densities above $7 \times 10^6$ c/mL. Clonal stability is evaluated by culturing the cells over a period of up 19 weeks with productivity measurements using the shake flask batch model approximately every two weeks.

3.3. Results:

Five cell populations, transfected with the DHFR/FoIR combination vector (VECTOR III) and three cell populations transfected with the reference vector (VECTOR IV) are generated and selected as described above. Productivity of the recovered cell pools in shaker flask batch cultures is summarized in table 5.

TABLE 7

Productivity of cells after one selection step, transfected with a DHFR/FoIR combination vector or a DHFR/Neo vector (reference). All values are mg/L.

|  | DHFR/FoIR Vector (VECTOR III) | DHFR/Neo Vector (VECTOR IV) |
| --- | --- | --- |
| Pool1 | 80 | 19 |
| Pool2 | 53 | 9 |
| Pool3 | 73 | 10 |
| Pool4 | 147 | Nd |
| Pool5 | 104 | Nd |

Use of the DHFR/FoIR combination vector (VECTOR III) leads to surprisingly good productivities already after only one selection step.

Pools are further processed by applying a FACS enrichment cycle and a second selection step with 10 fold increased MTX concentrations. Again very high pool productivities are obtained whereby the combination vector works as good as the co-transfection approach (see Table 8).

TABLE 8

Shake flask batch model: FACS enriched pools after 2$^{nd}$ selection step (50 nM MTX). All values are mg/L.

| Vector | Average pool productivity after FACS enrichment cycle and 2$^{nd}$ selection step (mg/L) |
|---|---|
| Co-transfection of VECTOR I and VECTOR II | 418 (n = 1) |
| Co-transfection of the FACS vectors VECTOR IV and VECTOR V | 797 +/− 87 (n = 2) |
| Transfection of the Combination-FACS-Vector (VECTOR III) | 709 +/− 400 (n = 2) |

Clones are generated by limiting dilution from a FACS enriched pool and expanded to 24-well plates for primary screening. The best producers are further expanded to shake flasks. Productivity is analyzed in shake flask batch cultures and compared to the results of the top clones obtained in previous experiments with the dhfr reference vector by FACS cloning.

The productivity of clones transfected with the combination VECTOR III in a shake flask batch model is significantly higher compared to the clones that were transfected with the reference VECTOR IV, which comprises only the DHFR gene (see Table 9)

TABLE 9

Shake flask batch model: Top 5 clones of reference dhfr vector (VECTOR IV) and combination vector (VECTOR III). All values are g/L.

| | vector/cloning | |
|---|---|---|
| Clone ranking | dhfr-FACS (VECTOR IV) | dhfr/foIR/FACS (VECTOR III) |
| 1 | 1.12 | 1.90 |
| 2 | 1.11 | 1.58 |
| 3 | 1.10 | 1.42 |
| 4 | 1.10 | 1.39 |
| 5 | 1.10 | 1.26 |

Clones transfected with VECTOR III are further analyzed for clonal production stability by thawing cryopreserved vials and monitoring productivity in a shake flask batch model. Productivity is monitored from week 5 after thawing to week 19 after thawing and compared to the productivity before cryopreservation. Clones are cultured under selective conditions while shake flask batch cultures are performed in media with high folic acid content (11.3 µM).

TABLE 10

Analysis of clonal production stability

| Clone (VECTOR III) | before Freezing | Week 5 (after thawing) | Week 8 (after thawing) | Week 12 (after thawing) | Week 15 (after thawing) | Week 17 (after thawing) | Week 19 (after thawing) |
|---|---|---|---|---|---|---|---|
| 14E3 | 1.06 | 1.16 | 1.17 | 1.17 | 0.92 | 1.02 | 1.08 |
| 15D1 | 1.12 | 1.09 | 1.10 | 1.13 | 0.84 | 0.89 | 0.91 |
| 15H7 | 1.42 | 1.32 | 1.36 | 1.34 | 1.09 | 1.15 | 1.13 |
| 15H9 | 1.58 | 1.68 | 1.69 | 1.50 | 1.22 | 1.35 | 1.29 |
| 17A10 | 1.26 | 1.16 | 1.14 | 1.07 | 0.90 | 1.00 | 1.00 |
| 17E7 | 1.90 | 1.79 | 1.82 | 1.76 | 1.56 | 1.78 | 1.76 |
| 17G3 | 1.16 | 1.13 | 1.14 | 1.14 | 0.87 | 0.94 | 0.95 |
| 17G11 | 1.26 | 1.19 | 1.21 | 1.14 | 0.98 | 0.96 | 1.03 |
| 19D1 | 1.39 | 1.15 | 1.18 | 1.11 | 0.86 | 0.85 | 0.87 |
| 19D7 | 1.17 | 0.95 | 1.02 | 1.05 | 0.82 | 0.90 | 0.97 |
| 19E11 | 1.14 | 1.01 | 1.04 | 1.08 | 0.88 | 1.06 | 1.00 |
| 20A7 | 1.07 | 1.00 | 1.00 | 0.98 | 0.84 | 0.89 | 0.91 |

Only one of the 12 analysed clones shows more than 25% loss in productivity over a period of 19 weeks, all others show high production stability.

IV. Example 4—Large Scale Production of Polypeptides with Transfected CHO Cells

The production of polypeptides in large scale can be done for example in wave, glass or stainless steel bioreactors. For that purpose the cells are expanded, usually starting from a single frozen vial, for example a vial from a Master Cell Bank. The cells are thawed and expanded through several steps. Bioreactors of different scale are inoculated with appropriate amounts of cells. The cell density can be increased by adding feed solutions and additives to the bioreactor. Cells are kept at a high viability for a prolonged time. Product concentrations in the reactor ranging from a few hundred milligrams per liter up to several grams per liter are achieved in the large scale. Purification can be done by standard chromatography methodology, which can include affinity, ion exchange, hydrophobic interaction or size exclusion chromatography steps. The size of the bioreactor can be up to several thousand liters volume in the final scale (see also e.g. F. Wurm, Nature Biotechnology Vol. 22, 11, 2004, 1393-1398).

The invention claimed is:

1. A process for producing a product of interest, comprising
   (a) providing a plurality of host cells, comprising
      (i) an introduced polynucleotide encoding a product of interest;
      (ii) an introduced polynucleotide encoding a first selectable marker (sm I); and
      (iii) an introduced polynucleotide encoding a second selectable marker (sm II), which differs from the first selectable marker (sm I);
      wherein the activity of the selectable marker (sm I) or (sm II) at least partially depends on the activity of the other selectable marker and wherein the selectable markers (sm I) and (sm II) are involved in folate metabolism; and
   (b) culturing said plurality of host cells under conditions selective for the selectable markers (sm I) and (sm II), thereby obtaining a host cell expressing the product of interest; and
   (c) culturing the host cell of (b) under conditions that allow for the expression of the product of interest.

2. The process according to claim 1, additionally comprising between steps (b) and (c) a step of
   selecting at least one host cell which expresses the product of interest.

3. The process according to claim 1, wherein said culturing is in a selective culture medium comprising folate and an antifolate.

4. The process according to claim 3, wherein the selective culture medium comprises folate in a concentration of 500 nM or less.

5. The process according to claim 3, wherein the selective culture medium comprises folate in a concentration of 500 nM or less, and wherein the selective culture medium comprises an antifolate in a concentration of 200 nM or less.

6. The process according to claim 3, wherein the selective culture medium comprises folate in a concentration of 100 nM or less.

7. The process according to claim 3, wherein the selective culture medium comprises an antifolate in a concentration of 500 nM or less.

8. The process according to claim 3, wherein the selective culture medium comprises an antifolate in a concentration of 200 nM or less.

9. The process according to claim 3, wherein the selective culture medium comprises folate in a concentration of 500 nM or less, and wherein the selective culture medium comprises an antifolate in a concentration of 500 nM or less.

10. The process according to claim 3, wherein the selective culture medium comprises folate in a concentration of 100 nM or less, and wherein the selective culture medium comprises an antifolate in a concentration of 200 nM or less.

11. The process according to claim 3, wherein the selective culture medium comprises folate in a concentration of 100 nM or less, and wherein the selective culture medium comprises an antifolate in a concentration of 500 nM or less.

12. The process according to claim 1, comprising at least one of the following steps:
    (a) isolating the product of interest from said cell culture medium and/or from said host cell; and
    (b) processing the isolated product of interest.

* * * * *

SEQUENCE LISTING

<160> NUMBER OF SEQ ID NOS: 3

<210> SEQ ID NO 1
<211> LENGTH: 257
<212> TYPE: PRT
<213> ORGANISM: Homo sapiens

<400> SEQUENCE: 1

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 2
<211> LENGTH: 255
<212> TYPE: PRT
<213> ORGANISM: Homo sapiens

<400> SEQUENCE: 2

Met Val Trp Lys Trp Met Pro Leu Leu Leu Leu Val Cys Val Ala
1               5                   10                  15

Thr Met Cys Ser Ala Gln Asp Arg Thr Asp Leu Leu Asn Val Cys Met
            20                  25                  30

Asp Ala Lys His His Lys Thr Lys Pro Gly Pro Glu Asp Lys Leu His
        35                  40                  45

Asp Gln Cys Ser Pro Trp Lys Lys Asn Ala Cys Cys Thr Ala Ser Thr
    50                  55                  60

```
Ser Gln Glu Leu His Lys Asp Thr Ser Arg Leu Tyr Asn Phe Asn Trp
 65                  70                  75                  80

Asp His Cys Gly Lys Met Glu Pro Ala Cys Lys Arg His Phe Ile Gln
                 85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
        115                 120                 125

Cys Lys Glu Asp Cys Gln Arg Trp Trp Glu Asp Cys His Thr Ser His
130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 3
<211> LENGTH: 245
<212> TYPE: PRT
<213> ORGANISM: Homo sapiens

<400> SEQUENCE: 3

Met Asp Met Ala Trp Gln Met Met Gln Leu Leu Leu Leu Ala Leu Val
 1               5                  10                  15

Thr Ala Ala Gly Ser Ala Gln Pro Arg Ser Ala Arg Ala Arg Thr Asp
                 20                  25                  30

Leu Leu Asn Val Cys Met Asn Ala Lys His His Lys Thr Gln Pro Ser
            35                  40                  45

Pro Glu Asp Glu Leu Tyr Gly Gln Cys Ser Pro Trp Lys Lys Asn Ala
        50                  55                  60

Cys Cys Thr Ala Ser Thr Ser Gln Glu Leu His Lys Asp Thr Ser Arg
 65                  70                  75                  80

Leu Tyr Asn Phe Asn Trp Asp His Cys Gly Lys Met Glu Pro Thr Cys
                 85                  90                  95

Lys Arg His Phe Ile Gln Asp Ser Cys Leu Tyr Glu Cys Ser Pro Asn
            100                 105                 110

Leu Gly Pro Trp Ile Arg Gln Val Asn Gln Ser Trp Arg Lys Glu Arg
        115                 120                 125

Ile Leu Asn Val Pro Leu Cys Lys Glu Asp Cys Glu Arg Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Ile Asn Glu Cys Pro Ala Gly Ala Leu Cys Ser
                165                 170                 175

Thr Phe Glu Ser Tyr Phe Pro Thr Pro Ala Ala Leu Cys Glu Gly Leu
```

-continued

```
              180                 185                 190
Trp Ser His Ser Phe Lys Val Ser Asn Tyr Ser Arg Gly Ser Gly Arg
        195                 200                 205

Cys Ile Gln Met Trp Phe Asp Ser Ala Gln Gly Asn Pro Asn Glu Glu
        210                 215                 220

Val Ala Lys Phe Tyr Ala Ala Ala Met Asn Ala Gly Ala Pro Ser Arg
225                 230                 235                 240

Gly Ile Ile Asp Ser
                245
```